(12) United States Patent
Sun et al.

(10) Patent No.: US 9,840,561 B2
(45) Date of Patent: Dec. 12, 2017

(54) HUMAN ANTI-HUMAN EPIDERMAL GROWTH FACTOR RECEPTOR ANTIBODY AND ENCODING GENE AND APPLICATION THEREOF

(71) Applicants: Shanghai serum biotechnology Co., LTD., Qingpu, Shanghai (CN); Institute of biotechnology, Academy of military medical sciences, PLA., Fengtai, Beijing (CN)

(72) Inventors: Zhiwei Sun, Beijing (CN); Shuang Wang, Beijing (CN); Jiuru Sun, Beijing (CN); Chang Zhang, Beijing (CN); Weiyi Qiu, Beijing (CN); Tiejiong Fan, Shanghai (CN)

(73) Assignee: Shanghai Saiyuan Bio-Technology Co., Ltd., Shanghai (CN)

( * ) Notice: Subject to any disclaimer, the term of this patent is extended or adjusted under 35 U.S.C. 154(b) by 0 days.

(21) Appl. No.: 14/436,845

(22) PCT Filed: Nov. 7, 2013

(86) PCT No.: PCT/CN2013/086661
§ 371 (c)(1),
(2) Date: Apr. 17, 2015

(87) PCT Pub. No.: WO2014/075576
PCT Pub. Date: May 22, 2014

(65) Prior Publication Data
US 2015/0274828 A1  Oct. 1, 2015

(30) Foreign Application Priority Data
Nov. 16, 2012 (CN) .......................... 2012 1 0465918

(51) Int. Cl.
| | | |
|---|---|---|
| *C07K 16/28* | (2006.01) | |
| *C07K 16/30* | (2006.01) | |
| *A61K 39/395* | (2006.01) | |
| *A61K 47/48* | (2006.01) | |
| *C12N 15/10* | (2006.01) | |
| *A61K 39/00* | (2006.01) | |
| *C07K 1/22* | (2006.01) | |

(52) U.S. Cl.
CPC .... *C07K 16/2863* (2013.01); *A61K 47/48561* (2013.01); *A61K 47/48569* (2013.01); *C07K 16/30* (2013.01); *C12N 15/1037* (2013.01); *A61K 39/39558* (2013.01); *A61K 2039/505* (2013.01); *C07K 1/22* (2013.01); *C07K 2317/21* (2013.01); *C07K 2317/24* (2013.01); *C07K 2317/31* (2013.01); *C07K 2317/565* (2013.01); *C07K 2317/622* (2013.01); *C07K 2317/73* (2013.01); *C07K 2317/76* (2013.01); *C07K 2317/92* (2013.01); *C07K 2319/55* (2013.01)

(58) Field of Classification Search
None
See application file for complete search history.

(56) References Cited

FOREIGN PATENT DOCUMENTS

| | | | |
|---|---|---|---|
| CN | 101029082 | A | 9/2007 |
| CN | 101058609 | A | 10/2007 |
| CN | 101619323 | A | 1/2010 |
| CN | 102993305 | A | 3/2013 |
| WO | WO 2012/066129 | A1 | 5/2012 |

*Primary Examiner* — Marianne P Allen
(74) *Attorney, Agent, or Firm* — Knobbe Martens Olson and Bear, LLP

(57) ABSTRACT

The present invention provides human anti-human epidermal growth factor receptor (EGFR) antibodies and their encoding genes and applications thereof. By gene engineering means and phage surface display technology, the present invention screens anti-human EGFR gene engineering single chain antibody from fully synthetic single chain human antibody library, and obtains the antibody variable gene sequence thereof, and based thereon, constructs intact human monoclonal antibody, to further obtain high-purity antibody protein. The binding affinity of the antibody of the present invention with human EGFR is no more than 1 nM, and the mutants affinity thereof is no more than 10 nM; and the identification of the immunity activity and bioactivity of antibodies protein IgG is completed, confirming that the antibody of the present invention has good bioactivity of inhibiting the tumor growth of EGFR expressing cell A431 tumor-bearing model mouse. The antibodies of the present invention provides specific antibody drugs for preventing and treating EGFR targeted tumor and other diseases such as inflammation and autoimmune diseases.

7 Claims, 10 Drawing Sheets

SEQUENCE LISTING

<160> NUMBER OF SEQ ID NOS: 22

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (4)..(4)
<223> OTHER INFORMATION: Xaa=Ala or Gly or Asn or Lys
<220> FEATURE:
<221> NAME/KEY: VARIANT
<222> LOCATION: (10)..(10)
<223> OTHER INFORMATION: Xaa=Ala or Val or Ile
<220> FEATURE:
<221> NAME/KEY: VARIANT
<222> LOCATION: (11)..(11)
<223> OTHER INFORMATION: Xaa=Ser or Tyr

<400> SEQUENCE: 1

Ser Gly Asp Xaa Leu Gly Asp Lys Tyr Xaa Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (3)..(3)
<223> OTHER INFORMATION: Xaa=Ser or Thr or Ala or Gly

<400> SEQUENCE: 2

Glu Asp Xaa Lys Arg Pro Ser
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa=Ser or Asn or Ala or Gly or Leu or Tyr or
    Gln
<220> FEATURE:
<221> NAME/KEY: VARIANT
<222> LOCATION: (2)..(2)
<223> OTHER INFORMATION: Xaa=Ser or Val or Ala or Leu
<220> FEATURE:
<221> NAME/KEY: VARIANT
<222> LOCATION: (5)..(5)
<223> OTHER INFORMATION: Xaa=Gly or Ala or Pro
<220> FEATURE:
<221> NAME/KEY: VARIANT
<222> LOCATION: (8)..(8)
<223> OTHER INFORMATION: Xaa=Gly or Ser

<400> SEQUENCE: 3

Xaa Xaa Trp Asp Xaa Asp Trp Xaa Met Pro
1               5                   10

<210> SEQ ID NO 4
<211> LENGTH: 5
<212> TYPE: PRT
<213> ORGANISM: Artificial Sequence -continued

```
<220> FEATURE:
<223> OTHER INFORMATION: Synthetic peptide

<400> SEQUENCE: 4

Ser Tyr Trp Ile Gly
1               5

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Xaa=Gly or Ser
<220> FEATURE:
<221> NAME/KEY: VARIANT
<222> LOCATION: (6)..(6)
<223> OTHER INFORMATION: Xaa=Gly or Ser

<400> SEQUENCE: 5

Xaa Ile Ile Tyr Pro Xaa Asp Ser Asp Thr Arg Tyr Ser Pro Ser Phe
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (9)..(9)
<223> OTHER INFORMATION: Xaa=Ala or Ser or Gly

<400> SEQUENCE: 6

Gly Ile Ile Tyr Pro Ser Asn Val Xaa Val
1               5                   10

<210> SEQ ID NO 7
<211> LENGTH: 108
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: VARIANT
<222> LOCATION: (32)..(32)
<223> OTHER INFORMATION: Xaa= Ala or Val or Ile
<220> FEATURE:
<221> NAME/KEY: VARIANT
<222> LOCATION: (33)..(33)
<223> OTHER INFORMATION: Xaa=Ser or Tyr
<220> FEATURE:
<221> NAME/KEY: VARIANT
<222> LOCATION: (51)..(51)
<223> OTHER INFORMATION: Xaa=Ser or Thr or Ala or Gly
<220> FEATURE:
<221> NAME/KEY: VARIANT
<222> LOCATION: (88)..(88)
<223> OTHER INFORMATION: Xaa=Ser or Asn or Ala or Gly or Leu or Tyr or
      Gln
<220> FEATURE:
<221> NAME/KEY: VARIANT
<222> LOCATION: (89)..(89)
<223> OTHER INFORMATION: Xaa= Ser or Val or Ala or Leu
<220> FEATURE:
```

```
<221> NAME/KEY: VARIANT
<222> LOCATION: (92)..(92)
<223> OTHER INFORMATION: Xaa=Gly or Ala or Pro
<220> FEATURE:
<221> NAME/KEY: VARIANT
<222> LOCATION: (95)..(95)
<223> OTHER INFORMATION: Xaa=Gly or Ser

<400> SEQUENCE: 7

Ser Tyr Glu Leu Thr Gln Pro Pro Ser Val Ser Val Ala Pro Gly Gln
1               5                   10                  15

Thr Ala Arg Ile Thr Cys Ser Gly Asp Xaa Leu Gly Asp Lys Tyr Xaa
            20                  25                  30

Xaa Trp Tyr Gln Gln Lys Pro Gly Gln Ala Pro Val Leu Val Ile Tyr
        35                  40                  45

Glu Asp Xaa Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Xaa Xaa Trp Asp Xaa Asp Trp Xaa Met
                85                  90                  95

Pro Val Phe Gly Gly Gly Thr Lys Leu Thr Val Leu
            100                 105

<210> SEQ ID NO 8
<211> LENGTH: 119
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (49)..(49)
<223> OTHER INFORMATION: Xaa=Gly or Ser
<220> FEATURE:
<221> NAME/KEY: VARIANT
<222> LOCATION: (54)..(54)
<223> OTHER INFORMATION: Xaa=Gly or Ser
<220> FEATURE:
<221> NAME/KEY: VARIANT
<222> LOCATION: (107)..(107)
<223> OTHER INFORMATION: Xaa=Ala or Ser or Gly

<400> SEQUENCE: 8

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Xaa Ile Ile Tyr Pro Xaa Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ile Ile Tyr Pro Ser Asn Val Xaa Val Trp Gly Gln Gly
            100                 105                 110

Thr Leu Val Thr Val Ser Ser
        115

<210> SEQ ID NO 9
```

```
<211> LENGTH: 327
<212> TYPE: DNA
<213> ORGANISM: Artificial Sequence
<220> FEATURE:
<223> OTHER INFORMATION: light chain variable region encoding gene of
      Ame55 single chain antibody

<400> SEQUENCE: 9
agctacgaac tgacccagcc gccgagcgtg tcggtggcgc cgggtcagac cgcgcgtatc    60
acctgctcgg gcgatgcgct gggcgataaa tacgcgagct ggtatcagca gaaaccgggt   120
caggcaccgg tgctggtgat ttacgaagat tctaaacgcc cgtctggcat cccggaacgc   180
tttagcggct cgaattcggg caacaccgcg accctgacca ttagcggcac ccaggcggag   240
gatgaggcgg actattactg ctcggtgtgg gatggcgact ggggatgcc tgtgtttggc    300 ggtggcacca aactgaccgt gctgggc                                       327

<210> SEQ ID NO 10
<211> LENGTH: 357
<212> TYPE: DNA
<213> ORGANISM: Artificial Sequence
<220> FEATURE:
<223> OTHER INFORMATION: heavy chain variable region encoding gene of
      Ame55 single chain antibody

<400> SEQUENCE: 10
gaagttcaac tggttcaaag tggtgcggaa gtgaagaaac cgggcgaaag tctgaaaatt    60
agttgcaaag ctctggttta ttcttttacg tcttattgga tcggctgggt tcgtcagatg   120
ccgggtaaag tctggaatg gatgggtatt atttatccgg gtgatagtga tacgcgttat    180
tctccgagtt ttcagggtca ggttactatt agtgcagata aaagcatcag caccgcgtat    240
ctgcagtgga gttctctgaa agcgagtgat accgcgatgt attattgcgc acgtggtatt    300
atttatcctt ctaatgtcgc tgtctggggt cagggcactc tggtgaccgt gtcgagc       357

<210> SEQ ID NO 11
<211> LENGTH: 49
<212> TYPE: DNA
<213> ORGANISM: Artificial Sequence
<220> FEATURE:
<223> OTHER INFORMATION: oligonucleotide

<400> SEQUENCE: 11
gaattagaat tcgccgccac catgcgaccc tccggacgg ccggggcag                 49

<210> SEQ ID NO 12
<211> LENGTH: 40
<212> TYPE: DNA
<213> ORGANISM: Artificial Sequence
<220> FEATURE:
<223> OTHER INFORMATION: oligonucleotide

<400> SEQUENCE: 12
gaatagctag ctccattcgt tggacagcct tcaagacctg                          40

<210> SEQ ID NO 13
<211> LENGTH: 47
<212> TYPE: DNA
<213> ORGANISM: Artificial Sequence
<220> FEATURE:
<223> OTHER INFORMATION: oligonucleotide

<400> SEQUENCE: 13
gaaggatcct taatggtgat gatggtgatg gctccattcg ttggaca                  47
```

<210> SEQ ID NO 14
<211> LENGTH: 45
<212> TYPE: DNA
<213> ORGANISM: Artificial Sequence
<220> FEATURE:
<223> OTHER INFORMATION: oligonucleotide

<400> SEQUENCE: 14
gcgcccctta agggcgtgca gtgcgaagtt caactggttc aaagc    45

<210> SEQ ID NO 15
<211> LENGTH: 31
<212> TYPE: DNA
<213> ORGANISM: Artificial Sequence
<220> FEATURE:
<223> OTHER INFORMATION: oligonucleotide

<400> SEQUENCE: 15
cggtgctagc gctcgacacg gtcaccagag t    31

<210> SEQ ID NO 16
<211> LENGTH: 44
<212> TYPE: DNA
<213> ORGANISM: Artificial Sequence
<220> FEATURE:
<223> OTHER INFORMATION: oligonucleotide

<400> SEQUENCE: 16
caagtgtaca ggatcatggg caagctacga actgacccag ccgc    44

<210> SEQ ID NO 17
<211> LENGTH: 28
<212> TYPE: DNA
<213> ORGANISM: Artificial Sequence
<220> FEATURE:
<223> OTHER INFORMATION: oligonucleotide

<400> SEQUENCE: 17
cggtaagctt ggtgccaccg ccaaacac    28

<210> SEQ ID NO 18
<211> LENGTH: 249
<212> TYPE: PRT
<213> ORGANISM: Artificial Sequence
<220> FEATURE:
<223> OTHER INFORMATION: Ame55 single chain antibody amino acid sequence

<400> SEQUENCE: 18

Ser Tyr Glu Leu Thr Gln Pro Pro Ser Val Ser Val Ala Pro Gly Gln
1               5                   10                  15

Thr Ala Arg Ile Thr Cys Ser Gly Asp Ala Leu Gly Asp Lys Tyr Ala
            20                  25                  30

Ser Trp Tyr Gln Gln Lys Pro Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Val Trp Asp Gly Asp Trp Gly Met
                85                  90                  95

Pro Val Phe Gly Gly Gly Thr Lys Leu Thr Val Leu Gly Ser Gly Gly
            100                 105                 110

```
Ser Thr Ile Thr Ser Tyr Asn Val Tyr Tyr Thr Lys Leu Ser Ser Ser
            115                 120                 125

Gly Ser Glu Val Gln Leu Val Gln Ser Gly Ala Glu Val Lys Lys Pro
        130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gly Ile Ile Tyr Pro Ser Asn Val Ala Val Trp Gly
225                 230                 235                 240

Gln Gly Thr Leu Val Thr Val Ser Ser
                245
```

```
<210> SEQ ID NO 19
<211> LENGTH: 747
<212> TYPE: DNA
<213> ORGANISM: Artificial Sequence
<220> FEATURE:
<223> OTHER INFORMATION: Ame55 single chain antibody nucleotide sequence

<400> SEQUENCE: 19
agctacgaac tgacccagcc gccgagcgtg tcggtggcgc cgggtcagac cgcgcgtatc      60
acctgctcgg gcgatgcgct gggcgataaa tacgcgagct ggtatcagca gaaaccgggt     120
caggcaccgg tgctggtgat ttacgaagat tctaaacgcc cgtctggcat cccggaacgc     180
tttagcggct cgaattcggg caacaccgcg accctgacca ttagcggcac ccaggcggag     240
gatgaggcgg actattactg ctcggtgtgg gatggcgact gggggatgcc tgtgtttggc     300
ggtggcacca aactgaccgt gctgggcagc ggcggctcga ccataacttc gtataatgta     360
tactatacga agttatcgag ctcgggcagc gaagttcaac tggttcaaag tggtgcggaa     420
gtgaagaaac cgggcgaaag tctgaaaatt agttgcaaag ctctggttat tcttttacg     480
tcttattgga tcggctgggt tcgtcagatg ccgggtaaag gtctggaatg gatgggtatt     540
atttatccgg gtgatagtga tacgcgttat tctccgagtt ttcagggtca ggttactatt     600
agtgcagata aaagcatcag caccgcgtat ctgcagtgga gttctctgaa agcgagtgat     660
accgcgatgt attattgcgc acgtggtatt atttatcctt ctaatgtcgc tgtctggggt     720
cagggcactc tggtgaccgt gtcgagc                                         747
```

```
<210> SEQ ID NO 20
<211> LENGTH: 109
<212> TYPE: PRT
<213> ORGANISM: Artificial Sequence
<220> FEATURE:
<223> OTHER INFORMATION: light chain variable region amino acid sequence
      of Ame55 single chain antibody

<400> SEQUENCE: 20

Ser Tyr Glu Leu Thr Gln Pro Pro Ser Val Ser Val Ala Pro Gly Gln
1               5                   10                  15

Thr Ala Arg Ile Thr Cys Ser Gly Asp Ala Leu Gly Asp Lys Tyr Ala
```

```
                    20                  25                  30

Ser Trp Tyr Gln Gln Lys Pro Gly Gln Ala Pro Val Leu Val Ile Tyr
            35                  40                  45

Glu Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Val Trp Asp Gly Asp Trp Gly Met
                85                  90                  95

Pro Val Phe Gly Gly Gly Thr Lys Leu Thr Val Leu Gly
            100                 105

<210> SEQ ID NO 21
<211> LENGTH: 119
<212> TYPE: PRT
<213> ORGANISM: Artificial Sequence
<220> FEATURE:
<223> OTHER INFORMATION: heavy chain variable region amino acid sequence
      of Ame55 single chain antibody

<400> SEQUENCE: 21

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ile Ile Tyr Pro Ser Asn Val Ala Val Trp Gly Gln Gly
            100                 105                 110

Thr Leu Val Thr Val Ser Ser
        115

<210> SEQ ID NO 22
<211> LENGTH: 118
<212> TYPE: PRT
<213> ORGANISM: Artificial Sequence
<220> FEATURE:
<223> OTHER INFORMATION: antibody heavy chain amino acid sequence of VH3
      germline gene family

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Thr Gly Thr Gly Gly Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95
Ala Arg Gly Trp Ser Trp Thr Gly Val Asp Pro Trp Gly Gln Gly Thr
            100                 105                 110
Leu Val Thr Val Ser Ser
        115
```

HUMAN ANTI-HUMAN EPIDERMAL GROWTH FACTOR RECEPTOR ANTIBODY AND ENCODING GENE AND APPLICATION THEREOF

TECHNICAL FIELD

The invention relates to the preparation and application of human genetic engineering antibody for treatment, and mainly relates to a specific anti-human epidermal growth factor receptor antibody and encoding gene and application thereof.

BACKGROUND ART

The epidermal growth factor receptor (EGFR) is a member of epidermal growth factor gene (erbB) family, and has significant influence in the development of various cancers, such as breast cancer, colon cancer, head and neck tumor, renal cancer, lung cancer, pancreatic cancer, prostatic cancer. Many domestic and overseas studies showed that the antibody against EGFR can inhibit EGFR signal transduction pathway by effectively blocking extracellular ligand binding, and has good therapeutic effect on human tumors expressed by various EGFR, especially head and neck squamous cell carcinoma (80%-100%), colorectal cancer (25%-77%), non-small-cell lung cancer (40%-80%) and pancreatic cancer. Currently, the epidermal growth factor receptor is one of deeply-studied and greatly-concerned tumor therapeutic targets, and it is one of research hotspots of current tumor treatment to use genetic engineering means to develop anti-EGFR monoclonal antibody.

At present, two anti-EGFR therapeutic antibodies have been approved by American FDA, viz. anti-EGFR mouse-human chimeric antibody Cetuximab (trade name: Erbitux) and anti-EGFR fully human antibody Panitumumab respectively, which are all used for the treatment of colorectal cancer and head and neck tumor. In 2005, anti-EGFR human antibody Nimotuzumab (trade name: TAIXINSHENG) was granted a new medicine certificate of Class 1 by Chinese Food and Drug Administration (CFDA). The antibody against the target being developed comprises human monoclonal antibody Pertuzumab, human antibodies Zalutumumab and Necitumumab, etc. Although the antigen epitopes to which they bind are different, they all can play a role in inhibiting biological functions mediated by EGFR.

Human antibody is the final development direction of a therapeutic antibody, and the use of human antibody in clinic can maximally reduce the immunogenicity of the antibody, prolong the half-life period of the antibody in vivo, and mediate immune regulation, ADCC and CDC effection by means of human immunoglobulin Fc fragment, and thereby enhance the biological effect of the antibody. The main means for development of the human antibody comprises antibody library technology and transgenic mouse technology. Currently, the large-capacity antibody library technology is well-established, especially the phage display antibody library technology has successfully made several fully human antibodies be sold on the market. In a constructed large-capacity antibody library, the semisynthetic antibody library of CAT company and fully synthetic antibody library of Marphosys AG company are the most representative and most successful examples. In particular, tens of candidate antibodies with development value have been obtained through the HuCAL GOLD technology of Marphosys AG company, and now there has been 17 projects entering clinical stage. The greatest advantage of such a technology is that it can optimize the antibody library via reasonable design, and the antibody framework gene thereof is a replaceable box structure, facilitating later optimization and modification of the antibody. Based on such an advantage, the HuCAL library so far has updated the antibody library thereof to third generation, of which the library capacity reaches $4.5 \times 10^{10}$, and from which high-affinity antibody with affinity up to pM level can be screened. Therefore, technologically, the use of antibody library technology to obtain therapeutic human antibody is well-established today, and is considered as one of the current most successful technical means for developing a therapeutic antibody. Through technology optimization and exploration, the applicant invented a high-effective method for DNA linkage and conversion, and applied it to construction of large-capacity phage antibody library. A large-capacity fully synthetic phage single chain human antibody resource library with library capacity up to $1.35 \times 10^{10}$ (ZL.200910091261.8) has been constructed, and multiple specific antibodies against different targets have been screened from the antibody library. The antibody Ame55 of the present invention is screened and obtained from the antibody library.

SUMMARY OF THE INVENTION

The present invention provides antibodies for treating and preventing diseases associated with EGFR expression, especially tumors expressing EGFR and autoimmune diseases.

The first purpose of the present invention is to provide amino acid sequences of human anti-EGFR antibodies and active fragments thereof.

The second purpose of the present invention is to provide genes encoding the antibody or the active fragments thereof described above.

The third purpose of the present invention is to provide applications of the antibody and the active fragments thereof described above in the drugs for treating malignant tumors expressing EGFR and autoimmune diseases.

Specific anti-human EGFR single chain engineered antibody (single chain variable fragment, svFv) of the present invention is screened from the large-capacity fully human synthetic single chain antibody library by multiple-time bio-panning through utilizing phage surface display technology. In an embodiment of the present invention, the light and heavy chain variable regions of the antibody described above are introduced into intact antibody transient expression vectors pABL and pABG1 for mammalian cells respectively, and transient secretion expression is performed to obtain IgG1 of Ame55 by co-transfecting HEK 293T cell.

The amino acid sequence pattern of the antibody variable region provided by the present invention is FR1-CDR1-FR2-CDR2-FR3-CDR3-FR4. Here, FR1-4 represent 4 framework regions, and CDR1-3 represent 3 hypervariable regions. FR1-4 may be isolated from a constant region sequence (e.g. amino acids commonly used in a light chain, a heavy chain, subclasses or subfamilies of a human immunoglobulin), isolated from individual antibody framework region, or produced by combining different framework genes, e.g. numerous human antibody framework region sequences included in libraries such as Kabat, etc.

There among, the heavy chain variable region is human immunoglobulin subgroup human heavy chain VH V family, and the light chain variable region is Lambda III family. With respect to the CDR regions of the light and heavy chains, a large number of mutants are obtained by alanine scanning and mutation of other similar amino acids, and the results regarding evaluation of mutants of light chains CDR1, CDR2 and CDR3 show that: the sequence of CDRL1 is SGDX1LGDKYX2X3 (SEQ ID NO 1). Here, X1 may be Ala, Gly, Asn, Lys, preferably Lys and Gly; X2 may be Val and Ile, preferable Ala; and X3 may be Ser and Tyr, preferably Ser. The sequence of CDR2L may be EDX1KRPS (SEQ ID NO 2). Here, X1 may be Ser, Thr, Ala and Gly, preferably Ser. The sequence of CDRL3 may be X1X2WDX3DWX4MP (SEQ ID NO 3). Here, X1 is Ser, Ala, Gly, Leu, Asn, Tyr and Gln, preferably Ser; X2 may be Val, Ser, Ala and Leu, preferably Ser or Ala; X3 may be Gly, Ala and Pro, preferably Gly; and X4 may be Gly and Ser, preferably Gly. The results regarding evaluation of mutants of heavy chains CDR2 and CDR3 show that: the sequence of CDRH2 is X1IIYPX2DSDTRYSPSFQ (SEQ ID NO 5). Here, X1 may be Gly and Ser, preferably Gly; X2 may be Gly and Ser, preferably Gly. The sequence of CDR3H is GIIYPSNVX1V (SEQ ID NO 6). Here, X1 may be Ala, Ser and Gly, preferably Ser or Ala. Alanine scanning is performed on the light and heavy chain CDR regions of the antibody, and the results show that the light and heavy chain CDR3, light chain CDR1 and heavy chain CDR2 are essential for the binding of antibody to EGFR, in which the change of only single amino acid can cause several times to tens of times of affinity change. Please see Example 5 for detail.

The human anti-human EGFR antibody provided by the present invention has a light chain variable region containing an amino acid sequence shown by SEQ ID NO 3.

In a further aspect, the light chain variable region thereof contains amino acid sequences shown by SEQ ID NO 1 and SEQ ID NO 2.

In still a further aspect, the light chain variable region thereof contains the amino acid sequence shown by SEQ ID NO 7.

Further, the human anti-human EGFR antibody provided by the present invention has a heavy chain variable region containing amino acid sequences shown by SEQ ID NO 5 and SEQ ID NO 6.

In a further aspect, the heavy chain variable region thereof also contains the amino acid sequence shown by SEQ ID NO 4.

In still a further aspect, the heavy chain variable region thereof contains the amino acid sequence shown by SEQ ID NO 8.

The human anti-human EGFR antibodies provided by the present invention include single chain antibody, Fab, mini antibody, chimeric antibody or intact antibody immunoglobulins IgG1, IgG2, IgA, IgE, IgM, IgG4, IgD.

The human anti-human EGFR antibody Ame55 provided by the present invention has the heavy chain variable region from $V_{H5}$, and has the light chain variable region from $V_{\lambda3}$, and the subtype the antibody is IgG1.

The human anti-human EGFR antibody provided by the present invention has the light chain variable region containing amino acid sequence shown by SEQ ID NO 3 and the heavy chain variable region containing amino acid sequence shown by SEQ ID NO 6.

The human anti-human EGFR antibody provided by the present invention has the light chain variable region containing amino acid sequence shown by SEQ ID NO 3 and the heavy chain variable region containing amino acid sequences shown by SEQ ID NO 5 and SEQ ID NO 6.

Preferably, the human anti-human EGFR antibody provided by the present invention has the light chain variable region containing amino acid sequence shown by SEQ ID NO 7 and the heavy chain variable region containing amino acid sequence shown by SEQ ID NO 8.

The human anti-human EGFR antibody provided by the present invention may bind to human EGFR with affinity of at least about $10^{-8}$ M. The antibody inhibits the binding of an EGFR ligand to human EGFR. The antibody binds to cells expressing EGFR; the cells may be human skin cancer cell, human liver cancer cell, human colon cancer cell, human cervical cancer cell, ovarian cancer cell, human lung cancer cell, bladder cancer cell, breast cancer cell, renal cancer cell, prostate cancer cell, head and neck neoplasm squamous cell, pancreatic cancer cell, synovial membrane fibroblast-like cell or keratinocyte cell.

The present invention provides the encoding genes of the mentioned antibodies.

Wherein, the nucleotide sequences of the gene encoding the light chain variable region are:

1) DNA sequence shown by SEQ ID NO 9;

2) nucleotide sequences hybridizing with the DNA sequence defined in 1) under a stringent condition and encoding the light chain variable region;

3) nucleotide sequences having more than 70% homology with the DNA sequence defined in 1) and encoding the light chain variable region.

In the present invention, "stringent condition" refer to: (1) hybridizing and eluting under lower ion strength and higher temperature, e.g. 0.2×SSC, 0.1% SDS, 60□; or (2) during hybridization, adding denaturant, such as 50%(V/V) formamide, 0.1% fetal calf serum/0.1Ficoll, 42□, etc.; or (3) hybridizing only when the homology between two sequences is at least above 70%, preferably at least above 80%, more preferably above 90%, more preferably above 95%.

Wherein the nucleotide sequences of the gene encoding the heavy chain variable region are:

1) DNA sequence shown by SEQ ID NO 10;

2) nucleotide sequences hybridizing with the DNA sequence defined in 1) under a stringent condition and encoding the heavy chain variable region;

3) nucleotide sequences having more than 70% homology with the DNA sequence defined in 1) and encoding the heavy chain variable region.

Moreover, considering codon degeneracy, the gene encoding the antibody according to the present invention may be, but not limited to, SEQ ID NOs 9 and 10, for example, the sequence of the gene encoding the antibody described above can be modified in the encoding region thereof without changing the amino acid sequence, to obtain a gene encoding the same antibody. A person skilled in the art can artificially synthesize a modified gene according to codon preference of a host expressing the antibody, so as to improve the expression efficiency of the antibody.

The present invention also provides an expression vector containing the genes described above.

The present invention provides a host bacterium, a host cell or an expression cassette containing the expression vector described above.

The present invention provides a method for preparing the antibody described above, comprising: screening anti-EGFR specific single chain antibody by using phage display antibody library technology to obtain antibody light chain and heavy chain variable region genes, and cloning the genes into a intact antibody expression vector, and performing intact antibody expression via mammalian expression system or other expression system to obtain the intact antibody protein thereof.

applications of the antibody described above in the preparation of drugs for treating diseases with EGFR as target is provided.

The drugs are anti-tumor drugs, anti-inflammatory drugs or drugs for treating autoimmune diseases.

The drugs or detection reagents containing the antibody described above also belong to the protection scope of the present invention.

Further, the drugs or detection reagents containing the antibody described above can be prepared by mixing another one or more antibodies with the antibody according to the present invention together to obtain a mixture preparation. Another one or more antibodies in the antibody mixture can be other antibodies against another antigen or different epitopes of EGFR. Researches proved that the combination of drugs against multiple targets related to a disease is an important research direction for therapeutic antibody, e.g., the combinations of antibodies against two targets EGFR and VEGFR and against two targets EGFR and ErbB2 have synergic anti-tumor effect (Pennell N A, Lynch T J. The Oncologist. 2009, 14: 399-411; Galer C E, Corey C L, Wang Z Y, et al. Head Neck. 2011, 33(2): 189-198; Kawaguchi Y, Kono K, Mimura K, et al. British J Cancer, 2007, 97,494-501); and the combination of antibodies against different epitopes of EGFR also has definite synergic anti-tumor effect (Pedersen M W, Jacobsen H J, Koefoed K, et al. Cancer Res. 2010, 70: 588-597), therefore, the mixture preparation of the antibody according to the present invention and other antibodies also falls into the protection scope of the present application.

The present invention also provides an antibody targeted drug, comprising the aforementioned human anti-human EGFR antibody linked to a cytotoxic agent in various forms.

The various linkage forms are antibody labeling, in-vitro cross-linking or molecular coupling.

The cytotoxic agent includes chemical molecules, radioactive isotopes, polypeptides, toxins and other substances having the properties of killing cells or inducing apoptosis.

The antibodies provided by the present invention are intact antibodies or various genetic engineering antibodies in other forms. For example, anti-EGFR antibody can be intact antibody or antibody fragment. The antibody molecule itself can be used for treatment and diagnosis. The antibody may be labeled, crosslinked or coupled and subjected to fusion expression with other proteins or polypeptide molecules to form a complex (such as cytotoxic substance, radioactive toxin and/or chemical molecule, etc.) for diagnosis and treatment.

The present invention further provides an independent gene encoding the antibody, an expression vector, a related control technology for vector transfecting host cell, host cell, antibody expression process and recovery of the antibody in cell culture supernatant. The present invention also provides a composition and pharmacologically acceptable delivering molecule or solution containing the antibody. The therapeutic composition of the present application is sterile and can be frozen under low temperature.

The present invention provides an anti-EGFR antibody, which can inhibit one or more bioactivities induced by EGFR. The antibody acts by blocking the binding of EGFR to the ligand thereof, acts by killing cells expressing EGFR, or acts by consuming the EGFR on cell surface via internalizing the complex formed by binding to EGFR. All interference functions possessed by EGFR antagonist should be equally considered as the purpose of the present invention.

The sequences shown by SEQ ID NOs.1-8 disclosed and claimed herein comprise "conserved sequence modification", i.e. nucleotide and amino acid sequence modification not obviously affecting and changing the binding feature of the antibody or the antibody containing the amino acid sequence. The conserved sequence modification comprises substitution, addition or deletion of nucleotides and an amino acid. The modifications can be introduced into SEQ ID NOs.1-8 by standard technologies in the art such as Site-directed mutagenesis and PCR-mediated mutagenesis. For example, an illustrative example of the conserved modifications is the modification achieved by performing alanine scanning on the antibody CDR region and performing amino acid mutation on partial sites, as described in the example of the present application. The conserved amino acid substitution comprises substituting an amino acid residue with an amino acid residue having similar side chain or other amino acid residues. In the art, the families of the amino acid residues having similar side chains have been defined. These families comprise amino acids with basic side chains (such as lysine, arginine, histidine), amino acids with acidic side chains (such as aspartic acid, glutamic acid), amino acids with uncharged polar side chains (such as glycine, asparaginate, glutamine, serine, threonine, tyrosine, cysteine, tryptophan), amino acids with nonpolar side chains (such as alanine, valine, leucine, isoleucine, proline, phenylalanine, methionine), amino acids with β branched side chains (such as threonine, valine, isoleucine), and amino acids with aromatic side chains (such as tyrosine, phenylalanine, tryptophan, histidine). Therefore, another amino acid residue from same side chain family is preferably used to substitute the nonessential amino acid residue in the human anti-EGFR antibody.

Therefore, the following antibodies are considered to fall into the scope of the present invention: the antibody encoded by the nucleotide sequence disclosed herein and/or the antibody containing the amino acid sequence disclosed herein, including the antibody basically encoded by a similar sequence modified by the conserved sequence, or containing a similar sequence modified by the conserved sequence.

The present invention provides a bispecific or multispecific molecule, i.e. a molecule comprising the antibody described above or antigen binding part thereof.

The present invention provides a fusion protein of an antibody with other proteins and/or polypeptides, comprising a complex of the aforementioned antibody provided by the present invention and other proteins or polypeptides molecules having a certain function.

Further, the fusion protein is prepared by linking the antibody gene to another antibody or antibody fragment, immunotoxin or cytokine gene to construct a recombinant expression vector, and obtaining a recombinant fusion protein molecule by mammalian cell or other expression system.

The antibody Ame55 described in the present invention has good treatment application prospect, which is mainly manifested as specific binding activity of the antibody with recombinant human EGFR and specific binding of the antibody with natural EGFR on surface of A431 cell. The antibody is proved to have good specificity through ELISA and immunohistochemical experiments; and the results of Western Blot proved that it only specifically bind to non-reducing EGFR, and does not bind or weakly bind to reducing EGFR.

The binding capability of the antibody to EGFR of various forms is detected using Biacore system, and the results show that the affinity $K_D$ of the antibody with recombinant EGFR extracellular region-Fc fusion protein is 0.23 nM (Biacore3000). The analysis by flow cytometry shows that the relative binding affinity of the antibody with EGFR on surface of A431 cell is higher than that of the marketed antibody TAIXINSHENG (nimotuzumab), and is equivalent to that of the marketed Erbitux. It is shown in the examples of the present invention that the binding affinity of the EGFR antibody of the present invention with human EGFR is no more than 1 nM, and the affinity of the mutant thereof is no more than 10 nM.

The antibody can inhibit the binding of Erbitux to EGFR in vitro, and Erbitux also can inhibit the binding of the antibody to EGFR. It is hinted that the antibody may be overlapped with Erbitux epitope in space structure. The antibody can competitively inhibit the binding of EGF to EGFR.

The antibody can obviously inhibit the migration activity of A431 cell. The results of cell scratch healing assay reveals that the antibody can obviously inhibit the scratch healing of A431 cell at the concentration of 5-50 µg/ml. Meanwhile, the antibody obviously inhibits the growth of A431 cell.

The antibody has obvious inhibition effect on the growth of A431 transplantation tumor, and when the antibody is administered to a mouse at the dosage of 1 mg/3d, the tumor inhibition rate can reach above 90%, and when administered to a mouse at the dosage of 0.2 mg/3d, the tumor inhibition rate can reach above 60%.

Mutant antibodies with affinity increased by over 5 times may be obtained by directed site-specific mutagenesis of the antibody, the in-vivo tumor inhibition activities of the mutant antibodies are further improved, and when some antibodies such as AmeA2, AmeA2C3, AmeA2C3-HI2, AmeA2C1, AmeA1C1 are administered at the dosage of 0.2 mg/3d, the tumor inhibition activity is more than 80%.

an anti-EGFR intact human antibody and a series of mutant antibodies with affinity unchanged or improved are obtained in the present application by screening using a large-capacity fully synthetic antibody library technology, and it is proved that the inventive antibodies all specifically bind to EGFR and inhibit the biological function thereof. By using the intact human anti-EGFR genetic engineering antibody variable region gene obtained above and the intact antibody gene possessing the antibody gene feature, the antibody can be expressed and produced in prokaryotic cells, yeast cells, eukaryotic cells and any recombinant systems; or by using any other genes re-constructed based thereon and containing the antibody gene, antibody products having EGFR inhibiting bioactivity are obtained; or by using the complex obtained via in-vitro labeling or crosslinking method, specific antibody drugs for clinically treating malignant tumors overexpressing or mutant-expressing EGFR and/or autoimmune diseases are prepared.

BRIEF DESCRIPTION OF THE DRAWINGS

FIG. 7 shows the competitive inhibition by Ame55 and Erbitux, wherein.

DESCRIPTION OF THE PREFERRED EMBODIMENTS

The following examples further describe the present invention, however, they should not be understood to limit the invention. The modifications and substitutions of the methods, procedures or conditions of the invention made without departing from the spirit and essence of the invention fall into the scope of the invention.

Unless particularly indicated, the technique means used in the examples are those well known to the skilled person in the art. All the materials, reagents and the like used in the following examples could be commercially available, unless otherwise expressly stated.

Example 1

Figure 16:
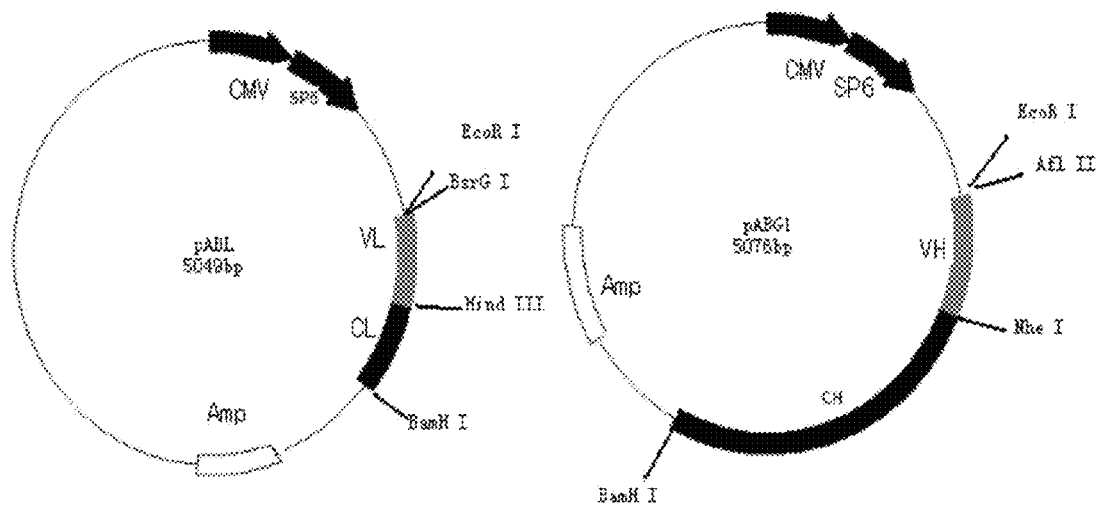
FIG. 16 is a schematic view of the vector for eukaryotic transient expression plasmid pABL and pABG1.

Screening of Specific Antibodies from a Large Capacity Phage Antibody Library I. Material and Method 1. Material: A large capacity fully synthetic phage single chain antibody library is constructed by the Chinese people's liberation army military academy of medical sciences (ZL200910091261.8), and the library capacity reaches $1.35 \times 10^{10}$. The antigens for screening the antibody library are purified EGFR-Fc fusion protein (at a concentration of 1 mg/ml) expressed in constructed mammalian cells and the strain is XL1-Blue (Stratagene, USA); the phage used is M13KO7 (Invitrogene, USA). The eukaryotic expression vectors pABG1 and pABL are stored in the room, and the structure information of the vector is shown in FIG. 16. The mammalian cell HEK293T cell is purchased from Invitrogene.

2. Method 2.1 Expression and Purification of EGFR-Fc Fusion Protein

Full-length extracellular region of EGFR was chosen as object, which was purchased from Sino Biological Inc. (NCBI sequence: NM_005228.3). The sense primer and reverse primer as shown in SEQ ID NO 11 and SEQ ID NO 12 were designed. PCR amplification was performed to obtain full-length genes of extracellular region, which were cloned into the eukaryotic expression vector pABG1 at the restriction enzyme sites EcoR I and Nhe I. Sequencing of the constructed recombinant plasmid was performed to identify the validity thereof and then the plasmid was extracted. HEK293T cells were transfected to perform transient expression, the supernatant after expression was purified using Protein A affinity column, and the protein was quantified for the purified product by Bradford method.

2.2 EGFR-his Expression and Purification

This step was accomplished on the basis of the method in section 2.1. The primer EGFRR1 (SEQ ID NO 13) was designed. The primers EGFRF and EGFRR1 were used to amplify the full-length genes of extracellular region of EGFR, which were cloned into the eukaryotic expression vector pABG1 at the restriction enzyme sites EcoR I and BamH I. Sequencing of the constructed recombinant plasmid was performed to identify the validity thereof and then the plasmid was extracted. HEK293T cells were transfected with the plasmid to perform transient expression, the supernatant after expression was purified using Ni+ affinity column, and the protein was quantified for the purified product by Bradford method.

2.3 Presentation of phage antibody library, which was performed according to the user instruction of recombinant phage selection of Pharmacia (Cat.NO.XY-040-00-05) with a minor modification. The details for modification are as follows:

Cryopreserved antibody library was taken and cultured in 200 mL 2xYTCG medium (glucose concentration of 0.5%) at 37° C. to $OD_{600}$=0.5. Helper phage M13KO7 was added at a ratio of MOI=20:1 and maintained at room temperature for 20 min. At 37° C., slowly shake cultivation was performed at 150 rpm for 1 h, kanamycin was added to reach the final concentration of 50 µg/ml, and IPTG was added to reach the final concentration of 0.1 mmol/L. At 30° C., shake cultivation was performed at 220 rpm for 10-12 h. In the next day, the cultured supernatant was collected by centrifugation and ⅕ volume of PEG8000 buffer (20% PEG+2.5 mol/L NaCl) was added therein. After mixing uniformly, the mixed supernatant was placed on the ice for 45 min for precipitating the phages. At 4° C., centrifugation was performed at 10000 g for 20 min, and the supernatant was discarded. The precipitation was resuspended in 5 ml PBS buffer containing 2% BSA and 15% glycerol, and the suspension was cryo-preseved at 70° C. for use.

2.4 Determination of Phage Titre

The monoclone of host bacteria (XL1-Blue) was selected and seeded in LB culture medium, followed by shake cultivation at 37° C. until logarithmic phase ($OD_{600}$=0.5). 50 µl prepared phage suspension was taken and gradiently diluted 10 folds with LB culture medium. The host bacterial cells at logarithmic phase were added into the suspension which had been diluted into a fold, followed by shake cultivation at 37° C. and at 150-180 rpm for 1 h. 100 or 200 µl of cultured bacteria liquid was coated onto LB plate and cultured at 37° C. overnight. In the next day, the number of colony was counted and the titre was calculated.

2.3 Bio-panning of anti-EGFR specific antibody, which was performed according to the user instruction of recombinant phage selection of Pharmacia (Cat.NO.XY-040-00-05) with a minor modification. The details for modification are as follows:

Recombinant protein antigen EGFR-Fc was diluted to 20 µg/ml with coating buffer, and the dilution solution was used to coat immune tubes, with 1 ml/tube. The immune tubes were coated at 4° C. overnight. In the next day, the immune tubes were washed with PBS twice, with 2 min for each, and then blocked with 2% BSA at 37° C. for 2 h. The prepared phage antibody library was blocked with blocking buffer (2% BSA, 0.1% Tween 20) at 37° C. for 30 min. The pre-blocked phage antibody library was added into the blocked immune tubes and maintained at 4° C. overnight. The solutions in the immune tubes were discarded and washing was performed. The first round of washing involves washing with PBST for 10 times, with 5 min/time, and washing with PBS for 5 times, with 5 min/time; the second round of washing involves washing with PBST for 15 times, with 5 min/time, and PBS for 10 times, with 5 min/time; the third round of washing involves washing with PBST for 15 times, with 5 min/time, and PBS+NaCl for 15 times, with 5 min/time. 1 ml 0.2 mol/L glycine-HCl (pH2.2) was added for elution. After the elution performed at room temperature for 10 min, the solution was immediately neutralized to pH 7.4 with 1 mol/L Tris. Direct infection with *E. coli* XL1-Blue at 37° C., and shake cultivation was performed at 150 rpm for 1 h. 2xYTCTG plate was coated with the residual bacterial solution and cultured overnight at 37° C. The bacterial colony was taken with liquid 2xYTCTG medium. An appropriate amount of bacterial solution was charged into 100 ml of 2xYTCTG liquid medium, and shake cultivation was performed at 37° C. until $OD_{600}$=0.5. The helper phages were added at a ratio of MOI=20:1 and maintained at room temperature for 20 min. Shake cultivation was performed at 150 rpm for 1 h at 30° C. The solution was added with the same volume of 2xYTCT medium, with kanamycin to a final concentration of 50 µ/ml, and with IPTG to a final concentration of 0.15 mM. Then the solution was cultivated on the shaker at 200 rpm under 30° C. for 10 h. The supernatant was collected via centrifugation and added with ⅕ volume of PEG8000 buffer solution (20% PEG +2.5 mol/L NaCl). After mixed homogeneously, the solution was placed on ice for 45 min to precipitate the phages. The solution was centrifuged at 10000 g for 20 min, and the supernatant was removed. The precipitation was resuspended in 5 ml PBS buffer solution containing 2% BSA and cryopreserved at −70° C. for use. 3 portions of phages ware determined for the titer, combined in proportion, and put into the next selection.

2.5 Identification of Positive Clones by Phage ELISA

The selected clones were placed in 96-well deep-well plates, with 250 μl 2xYTCTG medium per well. After shake cultivation at 37° C. until $OD_{600}$=0.5, 1×10$^8$ cfu helper phages was added and maintained at room temperature for 15 min Shake cultivation was performed at 37° C. and at 150 rpm for 1 h, and the same volume of 2xYTCTKI (kanamycin of 50 μg/ml, IPTG of 0.2 mmol/L) was added. Shake cultivation was performed at 30° C. overnight. In the next day, the supernatant was collected via centrifugation, added with BSA to a final concentration of 2%, added with Tween-20 to a final concentration of 0.1%, and maintained at 37° C. for 15 min for use. The antigen (EGFR) was diluted with coating solution to 1 μg/ml, added into 96-well assay plate, with 50 μl/well, for coating overnight at 4° C. In the next day, the coating solution was discarded. The assay plate was rinsed twice with PBST and once with PBS, 3 min for each rinse. The plate was blocked with 2% BSA+0.1% Tween-20 at 37° C. for 2 h, with 200 μl/well. The blocking solution was discarded, and then each well was added with blocked monoclonal phage antibody at 37° C. with 50 μl/well and maintained for 1 h. The liquid was discarded. The plate was rinsed twice with PBST and once with PBS, with 200 μl/well, 5 min for each rinse. HRP-labelled murine anti-M13 antibody was diluted with PBST at a dilution ratio of 1:5000. At the same time, BSA at a final concentration of 2% was added and the antibody was pre-blocked at 37° C. for 15 min. The pre-blocked murine anti-M13 antibody was added into the assay plate with 50 μl/well and maintained at 37° C. for 30 min. The liquid was discarded and the assay plate was rinsed twice with PBST and once with PBS, with 200 μl/well, 5 min for each rinse. The rinsing solution was discarded. OPD substrate developing solution was added, with 50 μl/well, and maintained at room temperature for development. The development was terminated by 2N $H_2SO_4$. The absorbance values were measured by microplate reader.

Coating buffer (pH 9.6): $Na_2CO_3$ 1.59 g, $NaHCO_3$ 2.93 g, supplemented with double distilled water to 1 L;

Blocking solution: 1xPBS+2% BSA+0.1% Tween 20; rinsing solution: 1xPBS +0.1% Tween 20;

OPD substrate diluting solution: 0.2M $Na_2HPO_4$ (28.4 g/L) 25.7 ml, 0.1M citric acid (19.2 g/L) 24.3 ml, distilled water 50 ml.

2.6 Conversion of Phage Single Chain Antibody into Intact Antibody:

Vectors pABG1 and pABL were used to clone the variable region genes of antibody heavy chain (e.g. SEQ ID NO 10) and light chain (e.g. SEQ ID NO 9) respectively. Primers H5F (SEQ ID NO 14) and HR(SEQ ID NO 15) were used to amplify variable region gene of VH5 respectively; and L3F (SEQ ID NO 16) and LR(SEQ ID NO 17) were used to amplify variable region gene of Vλ3. The variable region gene of Vλ3 was cloned into vector pABL using restriction enzyme cutting sites Bsr GI and HindIII. The variable region gene of VH5 was cloned into vector pABL using restriction enzyme cutting sites Afl II and NheI. E. coli DH5α was transformed with the recombinant plasmid. PCR of the bacterial solution and sequencing identification were performed on the recombinant plasmid, to obtain light and heavy chain expression vectors of the correctly constructed intact antibody. After extraction of the plasmid in large quantity, the HEK293T cells were tranfected with the light and heavy chains of the antibody at a molar ratio of 1:1, to perform the transient expression of the intact antibody, the supernatant after expression was purified by Protein A affinity column, and then the purified antibodies were subjected to the electrophoretic analysis and affinity and specificity assays.

II. Results

1. Selection and Identification of Ame55 Phage Antibody

The monoclonal antibodies obtained from the third selection were identified to obtain specific phage antibody. The nucleotide and amino acid sequences of Ame55 single chain antibody are shown as SEQ ID NO 18 and SEQ ID NO 19. The nucleotide sequences of light and heavy chain variable regions of Ame55 single chain antibody are shown as SEQ ID NO 9 and SEQ ID NO 10, respectively. The amino acid sequences of light and heavy chain variable regions of Ame55 single chain antibody are shown as SEQ ID NO 20 and SEQ ID NO 21, respectively.

Figure 1:
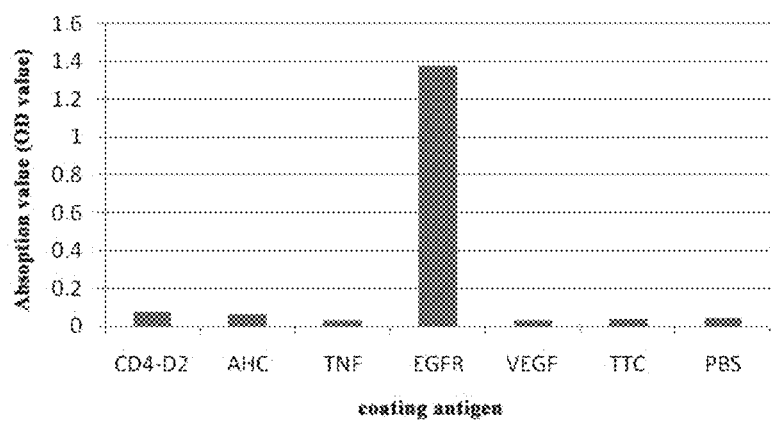
FIG. 1 shows analysis of the specificity of Ame55 phage antibody.

The specificity of Ame55 was analysed at the level of phage using EGFR-Fc as positive antigen and CD4-D2, AHC, TNF, VEGF, TTC, PBS as control antigen. The assay plate was coated at 4° C. overnight. The phage supernatant was added and the specific binding activity of Ame55 phage supernatant was tested by ELISA using HRP-labelled anti-M13 antibody as secondary antibody. The result showed that Ame55 only specially binds to EGFR-Fc. (FIG. 1)

2. Expression and Purification of the Intact Antibody

Figure 2:
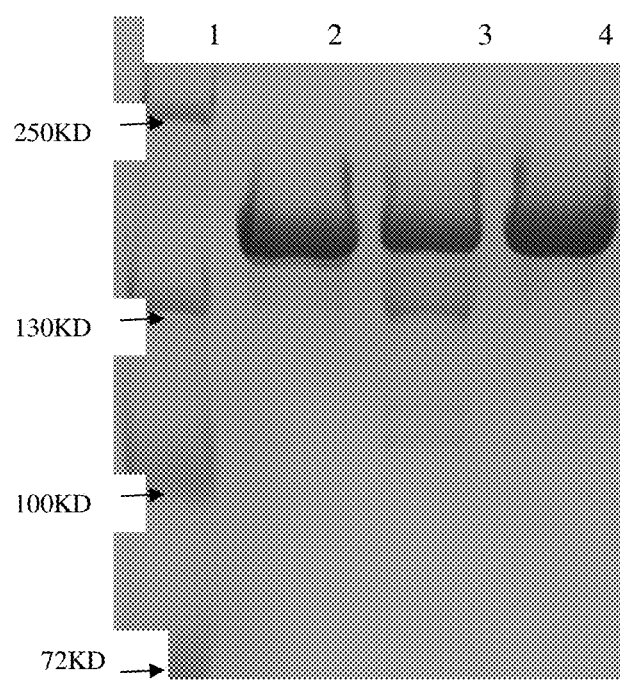
FIG. 2 shows a SDS-PAGE electrophoretogram of Ame55 treated by one-step purification of Protein A column, wherein, 1: Pr Marker; 2: Erbitux; 3: Ame55; 4: Nimotuzumab.

The variable region genes of light and heavy chains of phage antibody Ame55 were respectively cloned into the transient expression vectors pABL and pABG1 for intact antibody to construct the recombinant expression vectors for the intact antibody. The transient secretory expression of mammalian cells was accomplished by HEK293T cell transient expression system. The intact antibody protein samples were obtained by purification through Protein A column with a molecular weight of 150 KD. (FIG. 2)

Example 2

Assay of Binding Activity of Ame55

I. Material and Method

1. Material: human epidermal squamous cancer cells were purchased from Shanghai cell bank, Chinese academy of sciences; Erbitux(CT), a product from Merck & Co. Inc, Germany; Nimotuzumab(Hr-3) was an anti-EGFR human antibody marketed by Beijing Baitai Biotech Pharmaceuticals Co., Ltd.; Avastin (Bevacizumab, rhuMAb-VEGF) was purchased from Roche, Germany; CM5 chip was a product from GE; and the anti-human immunoglobulin Fc capture sensor and streptavidin sensor were purchased from FortéBio, Inc. (Shanghai). Recombinant human epidermal growth factor (EGF) was purchased from Sinobio Bio, Inc., Shanghai. FreeStyleTM293-F cell line, expression medium and transfection reagents were purchased from Invitrogen.

II. Method 2.1 Immunofluorescence Assay of Binding Activity of Antibodies to EGFR on A431 Cell Surface (1) A431 cells were seeded in 96-well plate with 10$^4$ cells/well.

(2) After culture overnight, the medium was discarded and then washing was performed with PBS twice.

(3) 5% skim milk powder (PBS formulation) was blocked at 37° C. for 1 h and then placed at 4° C.

(4) the primary antibody to be measured was diluted with 5% skim milk powder (PBST formulation) to 1 μg/ml, and pre-blocked at 37° C. for 30 min and then placed at 4° C. Erbitux (Ct) and Nimotuzumab (Hr-3), which are commercial drugs, were used as positive antibody control, and avastin (Avs) as negative antibody control.

(5) The blocking solution was discarded and the blocked antibody was added and incubated at 4° C. for 1 h.

(6) Washing was performed with PBST for 3 times at 240 rpm, with 3 min/time.

(7) The supernatant was discarded, FITC-labelled goat anti-human IgG secondary antibody which was pre-blocked by 5% skim milk powder was added, and bound at 4° C. for 30 min.

(8) Washing was performed with PBST for 3 times at 240 rpm, with 3 min/time.

(9) Observation was conducted under fluorescence microscope.

2.2 Western Blotting (1) Reducing and non-reducing SDS-PAGE gel electrophoresis were applied to EGFR-his antigen, and the gel concentrations for running were 10% respectively;

(2) the proteins were tranferred from gel into nitrocellulose membrane by semi-dry method. After the end of electrophoresis, the gel for electrophoresis was transferred to nitrocellulose membrane for 2 h via semi-dry electric transfer method at 20 mA. After the transfer to the membrane, the membrane was blocked with 5% skim milk at 37° C. for 2 h;

(3) after the membrane was blocked, the membrane were cut off and added with 10 μg/ml Ct, hR-3 and Ame55 respectively for binding at 4° C. overnight;

(4) washing was performed with TBST for 4 times, with 10 min/time;

(5) HRP-labelled goat anti-human IgG (which was pre-blocked at 37° C. for 30 min) diluted with 5% skim milk powder at 1:5000 was added, and incubated at 37° C. for 40 min;

(6) after incubation of the secondary antibody, washing was performed with TBST for 3 times, with 10 min/time.

(7) development: ECL luminous fluid was added thereto and development and exposure were performed in a dark room.

2.3 Measurement of Affinity of Antibody by Biacore 3000 System 10 mM NaAC were formulated with a pH of pH4.0, pH4.5, pH5.0 and pH5.5. The antibodies to be measured were diluted at appropriate times and pre-concentrated on CM5 chip. The NaAc solution with the optimal pH was selected as coating dilution solution, and the dilution concentration of the antibody was determined, which is most suitable for coating.

Coating: the antibodies to be measured were diluted with NaAc solution with the the optimal pH. The optimal dilution concentration was selected, one channel in CM5 chip was selected for coupling, wherein the target value of coupling antibody was 2000RU, and another channel was selected as control. The experimental condition included temperature of 25° C., flow rate of 20 μL/min and HBS-EP (pH7.4, Bia-Certified) as buffer solution. After the chip-coupling antibody reached the target value, the chip surface was blocked.

Analysis of regeneration conditions: 100 nM EGFR-Fc was gotten to flow through the surface of the chip, such that it binds to the antibodies on the surface of the chip. After stabilization, 10 mM glycine-HCl at pH 3.5, pH 2.5, pH 2.0, pH 1.5 and borate saline buffer at pH 8.5 flowed successively through the surface of the chip until the optimal regeneration effect was achieved, such that the optimal regeneration condition can be determined.

Dynamic analysis of binding of antibody to antigen: the concentration of antigen EGFR-Fc was measured by Broford method. The antigen was diluted with HBS-EP buffer solution. EGFR-Fc dilutions with different concentrations (5 different concentrations of dilutions were taken between 0-100 nM) were taken and gotten to flow the channels of antibodies to be measured and the channels of control antibody in a flow rate of 20 μL/min, with binding time of 3 min, stablizing time of 1 min and dissociation time of 15 min. Regeneration condition for each cycle included: 10 mM glycine-HCl, pH 1.5 and pH 8.5 of borate saline buffer, flow rate of 20 μL/min Each solution was regenerated for 30 s.

Calculation of affinity constant: the kenetic constant of binding of the antibody to antigen was calculated by fitting Langmuir binding model of the resultant sensorgram with the ratio of 1:1 using Bia-evalutation analysis software 4.

2.4 Flow Cytometry (1) A431 cells with EDTA trypsinization in good growth state were resuspended in pre-cool PBS, counted after washing, and formulated into a concentration of $6 \times 10^6$ cells/ml. the resultant solution was subpackaged into 1.5 ml centrifuge tubs, with 100 μL/tube, and the tubes were placed on ice.

(2) The antibody to be measured was diluted with pre-cool PBS to 150 μg/ml, 15 μg/ml, 1.5 μg/ml and 0.15 μg/ml. 100 μL of each dilution solution was taken and mixed with pre-cool cells respectively, and incubated on ice for 40 min.

(3) The resultant mixture was centrifuged in pre-cooled centrifuge at 4° C., the supernatant was drawn lightly, 1 ml pre-cooled PBS solution was added for washing for 3 times.

(4) Pre-blocked FITC-rabbit anti-human IgG secondary antibody diluted at a ratio of 1:100 was added into each tube and the tubes were incubated on ice for 30 min.

(5) Step (3) was repeated and washing was performed for 3 times.

(6) 500μL pre-cooled PBS solution was added into each tube with cells, blowed and beated lightly and uniformly, the samples were placed on the ice and the fluorometric analysis was performed by flow cytometer. The sample without antibody to be measured was used as control.

II. Result

1. Antibody Ame55 Specifically Binds to Non-Denatured EGFR.

Figure 3:
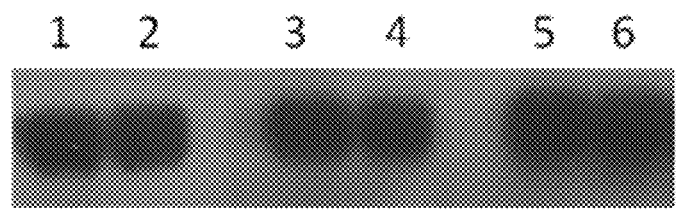
FIG. 3 shows the binding of Ame55 to EGFR identified by Western Blot, wherein, 1: non-denatured EGFR-Erbitux; 2: denatured EGFR-Erbitux; 3: non-denatured EGFR-Ame55; 4: denatured EGFR-Ame55; 5: non-denatured EGFR-Nimotuzumab; 6: denatured EGFR-Nimotuzumab.

Reducing and non-reducing SDS-PAGE gel electrophoresis were applied to EGFR-his. Western blot was performed using 10 μg/ml of Ame55, Erbitux and Nimotuzumab as primary antibodies and HRP-labelled goat anti-human IgG as secondary antibody respectively. The results are shown in FIG. 3. Ame55 only specifically binds to non-denatured EGFR.

2. Ame55 Specifically Binds to EGFR on A431 Cell Surface.

Figure 4:
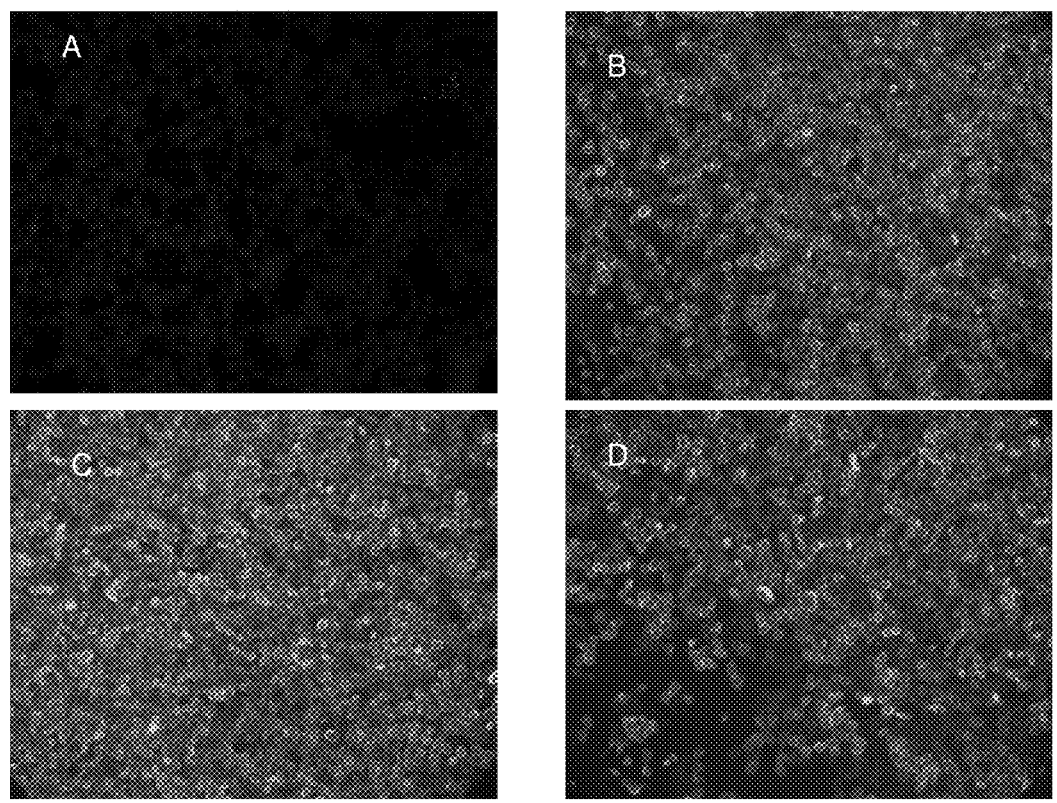
FIG. 4 includes images showing the indirect immunofluorescence assay for the cytomixis of Ame55 and A431, wherein, A: avastin-A431; B: Ame55-A431; C: Erbitux-A431; D: Nimotuzumab-A431.
Figure 5A:
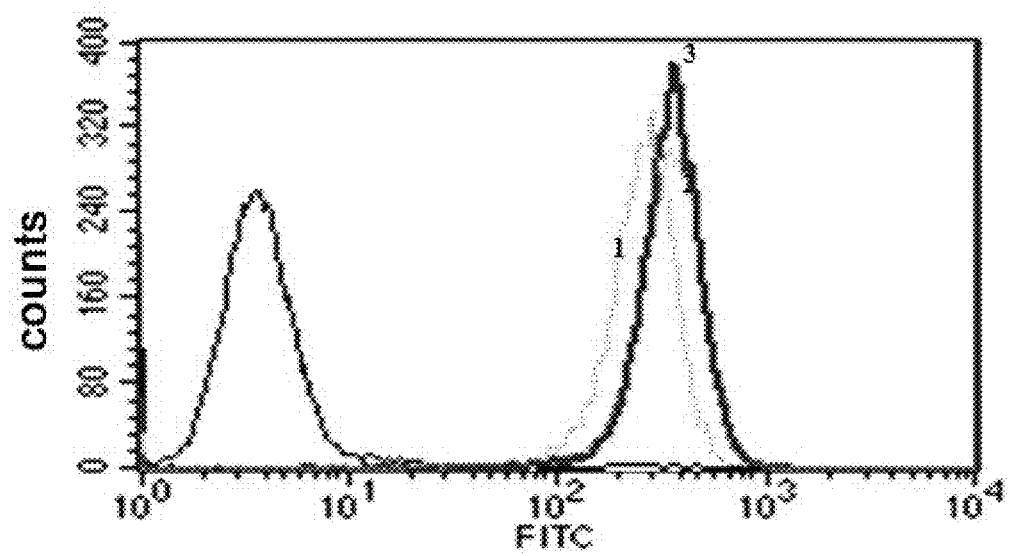
FIG. 5 is a graph showing the analysis of binding of Ame55 to EGFR on A431 cell surface by flow cytometry, in FIG. 5A, antibody concentration: 3 µg/ml.
in FIG. 5B: antibody concentration: 0.3 µg/ml.
in FIG. 5C: antibody concentration: 0.03 µg/ml, 1 represents antibody Nimotuzumab; 2 represents antibody Ame55; 3 represents antibody Erbitux.
Figure 5B:
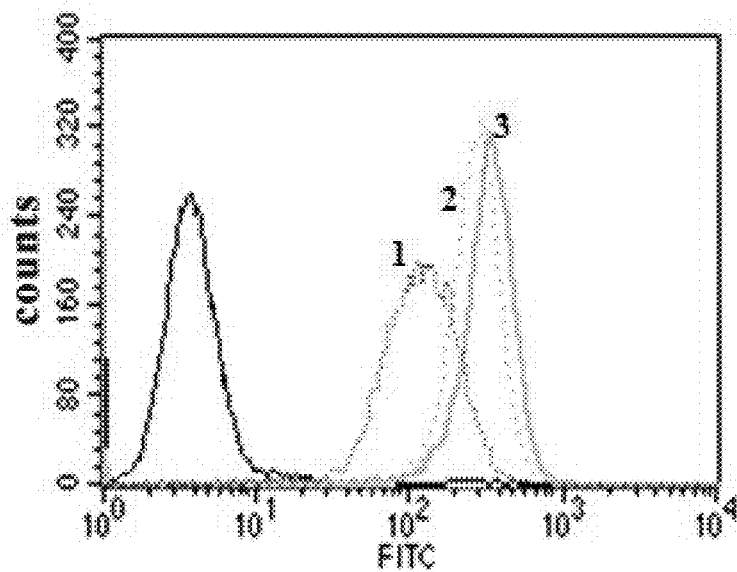
Figure 5C:
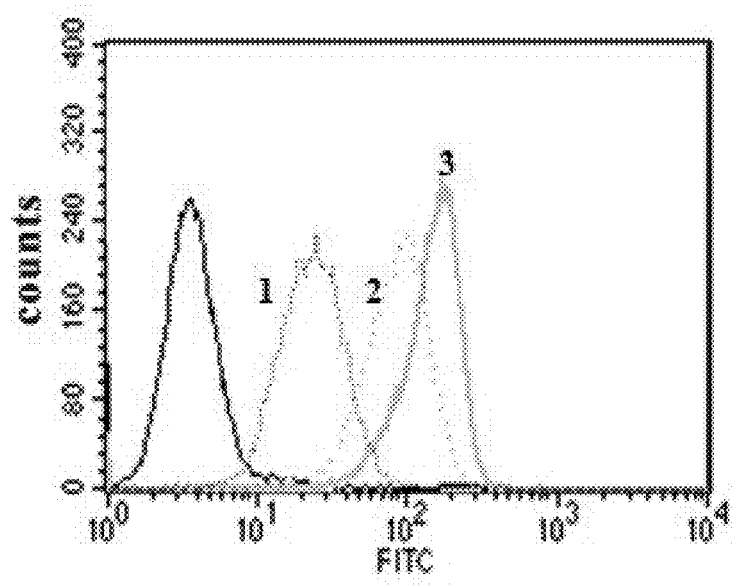

Cellular immune fluorescence assay was performed using A431 cell expressing EGFR as antigen, Amet55, unrelated antibody Avastin, control antibody Erbitux and Nimotuzumab as primary antibodies, and goat anti-human IgG as secondary antibody. The results are shown in FIG. 4, and indicates that Ame55 (B in FIG. 4), positive control antibody Erbitux (C in FIG. 4) and Nimotuzumab (D in FIG. 4) can specifically bind to EGFR on A431 cell surface, but negative control antibody Avastin (A in FIG. 4) did not bind. The binding of Ame55 to A431 cells was further analyzed by flow cytometry. The result indicates that this antibody, in a certain concentration range, binds to A431 cells in a dosedependent way. In the case of a concentration of less than 1 µg/ml, the fluorescence intensity of Ame55 is between control Erbitux and Nimotuzumab (FIG. 5A, FIG. 5B and FIG. 5C).

3. Measurement of Affinity Ame55 for EGFR-Fc by Biacore 3000.

Figure 6:
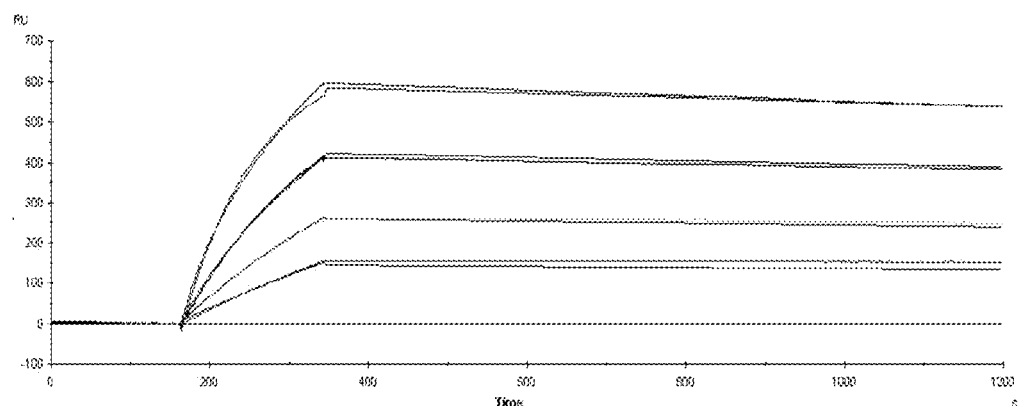
FIG. 6 is a graph showing affinity of ame55 to EGFR-Fc as measured by Biacore.

Ame55 was coated on the surface of CM5 chip. Affinity of Ame55 for EGFR-Fc was measured by Biacore 3000 system using different concentrations of EGFR-Fc as mobile phase. The results are shown in FIG. 6. The affinity constant $K_D$ after fitting is 0.231 nM, wherein Ka=$4.21 \times 10^5$, Kd=$9.73 \times 10^{-5}$.

Example 3

In Vitro Activity and Epitope Analysis of Ame55

I. Method
1 Inhibition Assay of Antibody Competitive Binding

Ame 55 as stationary phase was coated on CM5 chip, wherein the conditions for coating and regeneration are shown in the method of Example 2. 50 nM EGFR-Fc as first mobile phase was gotten to flow through the sample channel with duration of 3 min Upon washing with PBS-T for 3 min, 1000 nM of Erbitux as second mobile phase was gotten to flow through the sample channel with duration of 3 min and the sample channel was then washed with PBST for 3 min. Furthermore, the above experiment was performed again using 1000 nM of Ame55 as the second mobile phase, which is used as self-competitive inhibition control. Likewise, the above experiment was repeated using Erbitux as stationary phase.

2. Competitive Inhibition Assay of Binding of EGR to EGFR

EGF was coated at 1 µg/well in 96-well plate overnight at 4° C. Ame55, the positive control antibody Erbitux and unrelated control antibody (anti-IL-6R antibody selected in the present invention) were mixed with 2.5 µg/well of EGFR-Fc at a molar ratio of 3:1, 2:1 and 1:1 respectively, and pre-blocked at 37° C. for 30 min, and were added into blocked EGR-coating ELISA plate, for binding at 37° C. for 1 h. Washing was performed with PBST for 3 times and with PBS once, with 5 min/time. The pre-blocked HRP-labelled goat anti-human IgG was used as secondary antibody and reacted at 37° C. for 30 min After washing with PBST and PBS, OPD substrate developing solution was added for development. The reaction was stopped by addition of 2N $H_2SO_4$, and the absorbance value was measured at $OD_{450\ nm}$.

3. A431 Cell Scratch Healing Assay

Straight lines were marked at the bottom of 6-well plate, for quinquesection of each well. A431 cells were seeded in the marked 6-well plate with $10^5$ cells/well. When the cells entered into logarithmic phase, the surface of cells was marked with line perpendicular to the straight lines using 200 µL of pipette. After marking, the surface was washed twice with PBS, and each well was added with the antibody Ame55 to be measured, positive control antibody Erbitux and negative control antibody Adalimumab (Abbott, USA) until a final concentration of 25 µg/ml was reached. A blank well was set up as blank control. At the observation time of 0 h, 12 h and 24 h, the fixed location was maked with straight lines and the photos are taken for the dynamic process.

4. A431 Cell Growth Inhibition Assay 1) seeding of the cells: the A431 cells were trypsinized, blown fully and counted, and the cell concentration was adjusted to 5000 cells/ml with 1640 culture medium containing 0.5% new-born calf serum, added into 96-well plate with 200 µL per well (finally 800-1000 cells were uniformly distributed in each well), and incubated at 37° C. and at 5% $CO_2$ for 24 h until cells completely extended to adherence;

2) Culture upon adding the antibody to be measured: the cell supernatant in the 96-well plate was discarded, and the palate was washed with PBS once. 200 nM of Erbitux(CT), Nimotuzumab (hR3) and Ame55 were prepared, and PBS was used as control, followed by adding them into 96-well plate with 200 µl/well 3 multiple-wells for each concentration. 5 pieces of 96-well plates were added in parallel, cultured at 37° C. under 5% $CO_2$, and then the solutions were exchanged on day 3 and 5 respectively. One culture plate was selected randomly for staining on day 0, 3, 4, 5, 6 and 7.

3) Crystal violet staining: the medium in the 96-well plate was removed and the plate was washed once with PBS; each well was added with 100 µL 4% paraformaldehyde and maintained for 15 min at room temperature for immobilization; the formaldehyde was removed and 0.5% crystal violet solution diluted with PBS (which was formed by diluting 5% crystal violet solution formulated with absolute ethyl alcohol into 10 fold) was added, with 100 µL/well, then the plated was maintained at room temperature for 15 min for staining; the crystal violet solution was removed and the plate was immerged into tap water and washed for several times; the plate was immerged into distilled water at room temperature, and washed on the horizontal shaker at 560 r/min for 15 min; the moisture was removed and the plate was dried overnight.

4) Cell density determination: the 6 96-well phates on Day 1 to 7 were collected for decoloration and determination of OD value for the same batches. 200 µL sorenson's solution was added into each well; the plates were placed in horizontal shaker at 400 r/min for 30 min for decoloration; 100 µL solution was taken from each well and added into a new 96 well-plate, and the absorbance value was measured at 590 nm with absorbance value at 630 nm as internal reference. The cell growth curve was plotted.

Sorenson's formulation method: Solution A: 8.967 g natrium citricum was dissolved in 305 ml ultrapure water; Solution B: 195 ml 0.1N HCl (1.6 ml 38% HCl was added in 193.4 ml ultrapure water, which is known as "addition of acid into water"); Solution C: 500 ml 95% ethyl alcohol (475 ml absolute ethyl alcohol was added with 25 ml ultrapure water); Solution A+B+C was mixed up to a total volume of 1 litre.

II. Result
1. Competitive Inhibition of Binding of Ame55 and Erbitux to EGFR

Figure 7A:
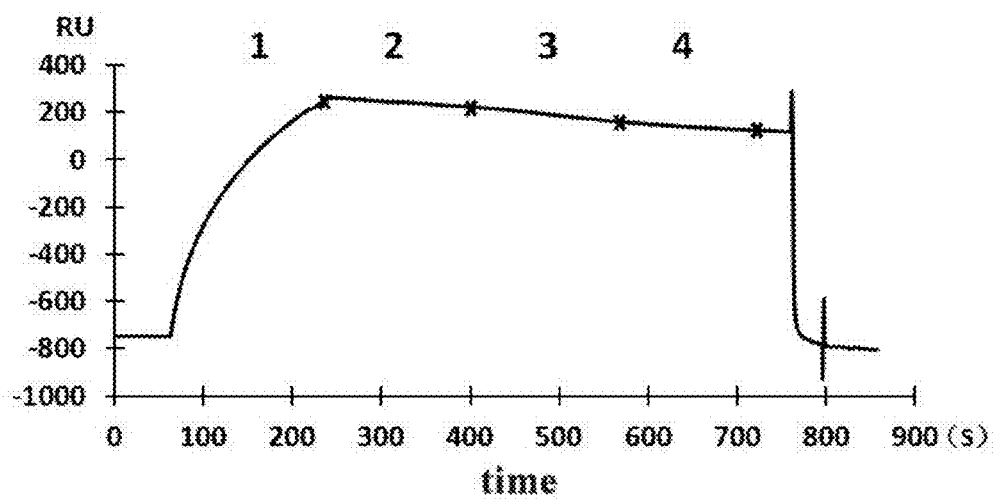
FIG. 7A: 1: EGFR-Fc binding; 2: PBST washing; 3: Ame55-binding; 4: PBST washing.
Figure 7B:
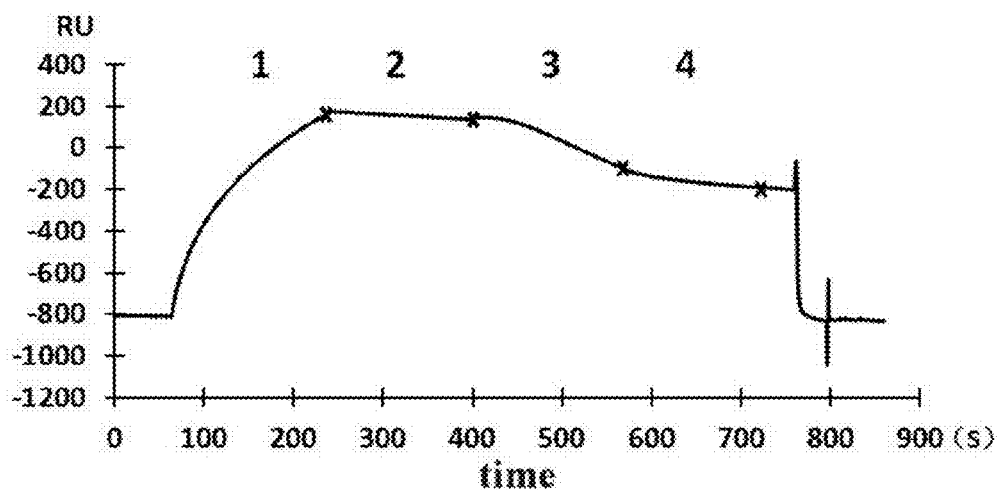
FIG. 7B: 1: EGFR-Fc binding; 2: PBST washing; 3: Erbitux-binding; 4: PBST washing.
Figure 7C:
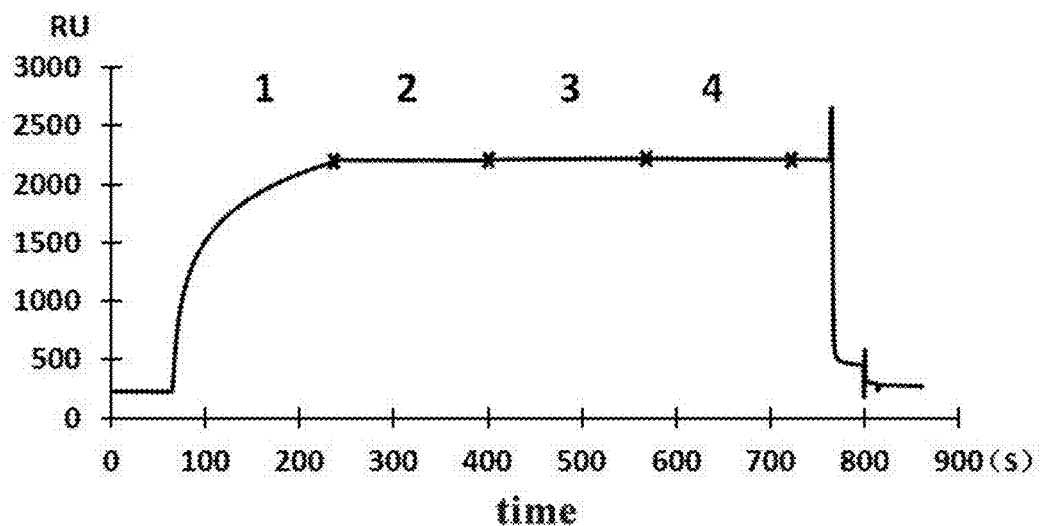
FIG. 7C: 1: EGFR-Fc binding; 2: PBST washing; 3: Erbitux-binding; 4: PBST washing.
Figure 7D:
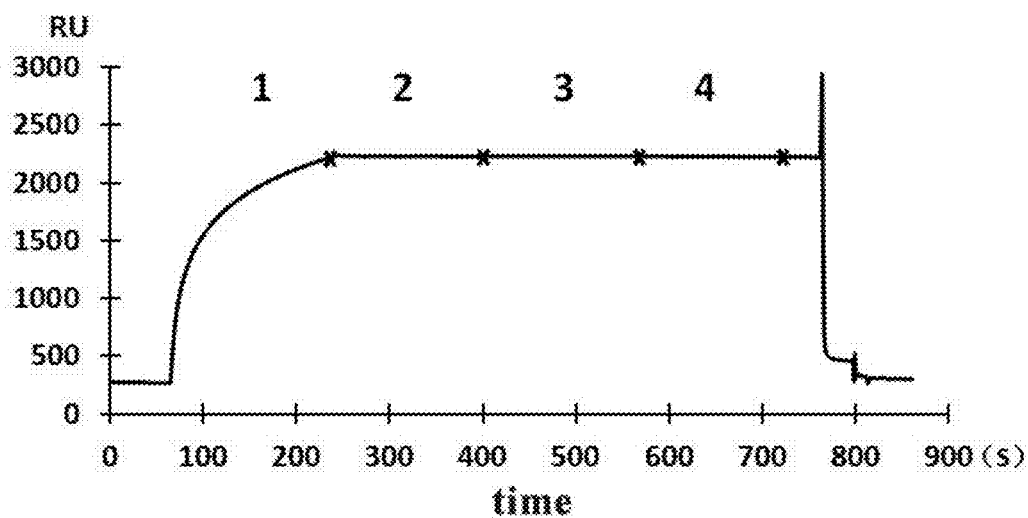
FIG. 7D: 1: EGFR-Fc binding; 2: PBST washing; 3: Ame55-binding; 4: PBST washing; for FIG. 7A and FIG. 7B, the stationary phase is Ame55, for FIG. 7C and FIG. 7D, the stationary phase is Erbitux.

The epitopes of two antibodies were analyzed preliminarily, the condition for analysis included: using Ame55 as stationary phase and EGFR as first mobile phase (1), washing with PBST for a period of time (2), using Ame55(A) and Erbitux (B) as second mobile phase (3), then washing again with PBST (4); on the contrary, using Erbitux as stationary phase and EGFR as first mobile phase (1), washing with PBST for a period of time (2), using Ame55(D) and Erbitux (C) as second mobile phase (3), then washing again with PBST (4). The results (see FIGS. 7A, 7B, 7C and 7D) indicate that EGFR bound to Ame55 can not further bind to Erbitux (FIGS. 7B and 7A show self-inhibition control of Ame55). That is, Ame55 can inhibit the binding of EGFR to Erbitux. On the contrary, upon binding to Erbitux, EGFR no longer binds to Ame55 (FIGS. 7D and 7C show self-inhibition control of Erbitux). That is, Erbitux can also inhibit the binding of EGFR to Ame55. The result reveals that there may be competitive inhibition of antigen epitopes between two antibodies. It is probably because the two antigen epitopes have highly similar or identical structure.

2. Competitive Inhibition of Binding of EGF to EGFR by Ame55

Figure 8:
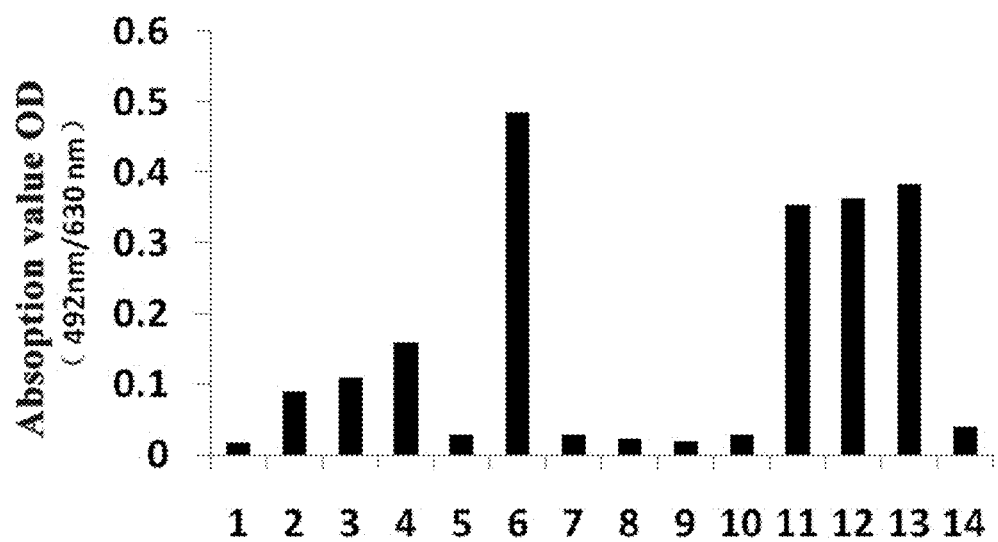
FIG. 8 is a graph showing the competitive inhibition of the EGR binding to EGFR by Ame55. 1: blank control; 2: the molar ratio of Ame55 to EGFR is 3:1; 3: the molar ratio of Ame55 to EGFR is 2:1; 4: the molar ratio of Ame55 to EGFR is 1:1; 5: Ame55; 6: EGFR; 7: the molar ratio of Erbitux to EGFR is 3:1; 8: the molar ratio of Erbitux to EGFR is 2:1; 9: the molar ratio of Erbitux to EGFR is 1:1; 10: Erbitux; 11: the molar ratio of unrelated antibody control to EGFR is 3:1; 12: the molar ratio of unrelated antibody to EGFR is 2:1; 13: the molar ratio of unrelated antibody to EGFR is 1:1; 14: unrelated antibody control.

The competitive inhibition of binding of EGF to EGFR by Ame55 was analyzed by competitive ELISA. The result indicates that Ame55 significantly inhibits the binding of EGF to EGFR when a ratio of EGFR to antibody is 1:1, 1:2 and 1:3, but the negative control has no inhibition effect. The inhibitary activity of Ame55 was less than that of Erbitux as control at the same concentration (see FIG. 8).

3 Inhibition of A431 Cell Migration by Ame55

Figure 9:
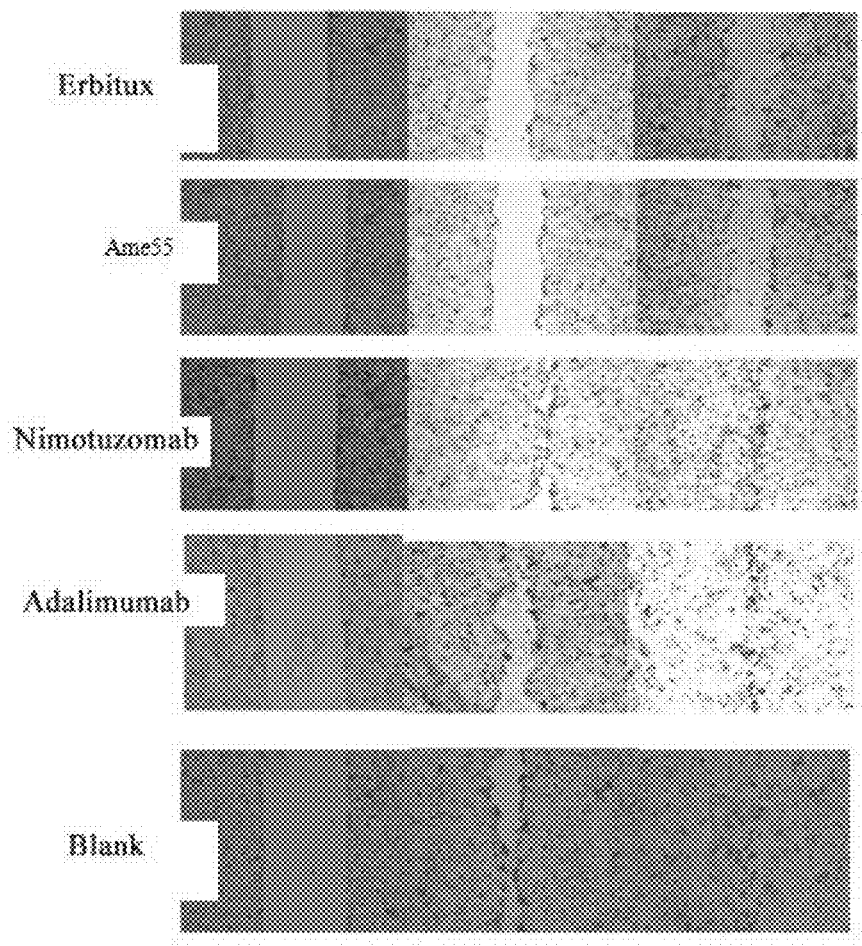
FIG. 9 is a graph showing the inhibition of Ame55, Erbitux, Nimotuzumab, Adalimumab and blank control on migration ability of A431 cells.
Figure 10:
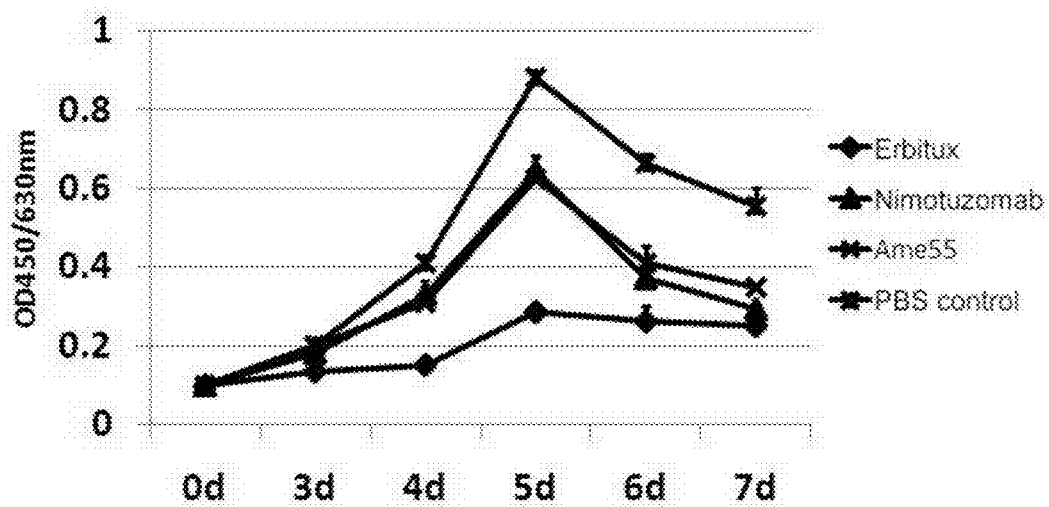
FIG. 10 is a graph showing the inhibition of Ame55, Erbitux, Nimotuzumab and PBS control on A431 cell growth.

As described for method 3 in the example, 25 μg/ML of experimental antibody group was dynamically observed for 24 h at fixed sites for the cell scratch healing (FIG. 9). For the inhibition of A431 cell migration, Ame55 exhibits the same inhibitory activity as Erbitux, whereas another negative control antibody Adalimumab, a commercial available antibody drug against TNFα, has no inhibitory activity on the A431 cell migration. The results indicate that, in FIG. 10, Ame55 does have the function of inhibiting biological activity of EGFR, revealing that it may have good effect in the therapeutic application of clinical metastases.

4 Inhibition of A431 Cell Growth by Ame55

The cells expressing EGFR, such as A431, act on the EGFR by autocrine EGF and therefore activate downstream pathway, which leads the dephosphorylation of receptor and promote cell growth and migration. Accordingly, the effect of Ame55 on the growth of cell expressing EGFR was further evaluated by A431 cell proliferation assay, and the cell growth tendency was observed continuously. The assay was performed as described for method 4 in the example. The results indicate that, in FIG. 10, Ame55 has an inhibition effect on A431 cell growth, but the inhibition degree of Ame55 is less than that of control antibody Erbitux, and is comparable to another control antibody Nimotuzumab.

Example 4

Detection of In-Vivo Tumor Inhibition Activity of Ame55

47 female nude mice (about 20 g) were subcutaneously inoculated at back with 100 μL of A431 cell at a concentration of $5 \times 10^7$. When the tumor grew to 50-150 $mm^3$, the mice were weighed, the tumor size was measured and grouped into 4 groups, i.e. normal saline group, Erbitux group, Adalimumab group and Ame55 group respectively, wherein Erbitux is a marketed anti-EGFR monoclonal antibody and was set as positive control; Adalimumab is a marketed anti-TNFα antibody drug and was set as negative control; and the normal saline was set as tumor-bearing control. The dose of antibody for administration was 1 mg/mouse, once every 3 days, and before each administration, the mice were weighed and the tumor size was measured. The tumor calculation method is: π/6*long diameter*short $diameter^2$. After 36 days, the mice were sacrificed to collect the tumors, the tumors were weighed, and then statistical analysis was performed.

Figure 11:
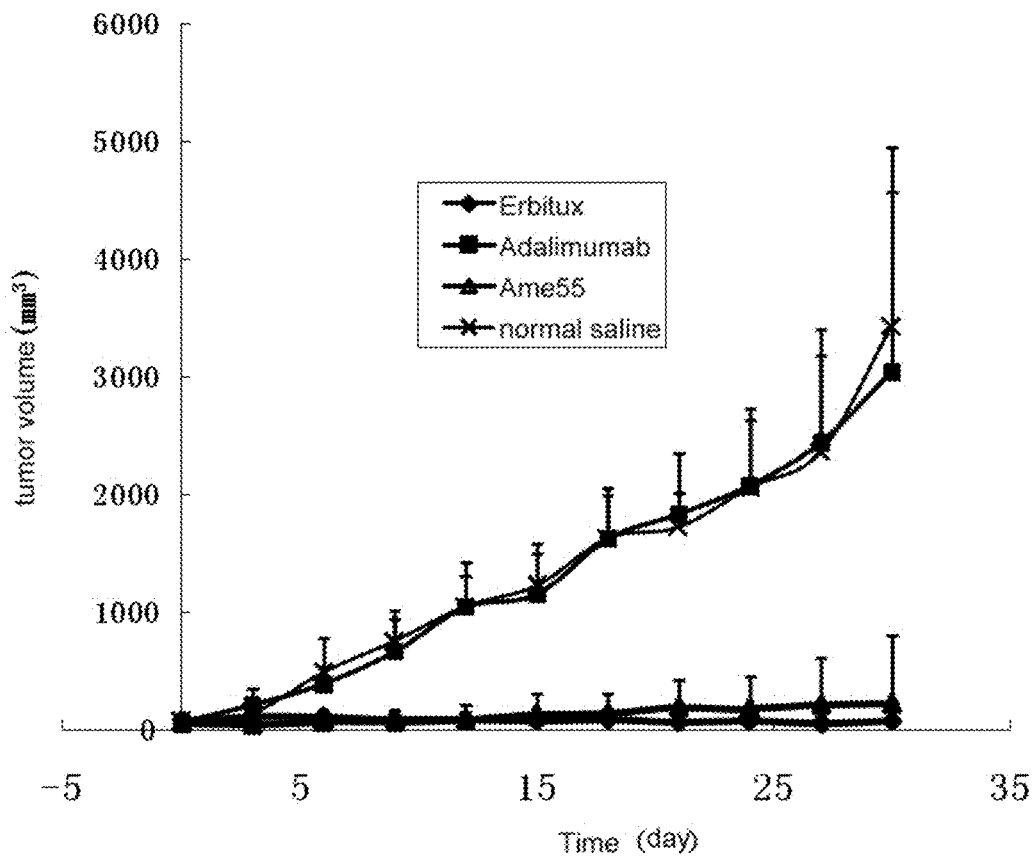
FIG. 11 is a graph showing the inhibition of Ame55 on tumor growth in A431 tumor-bearing mic.
Figure 12:
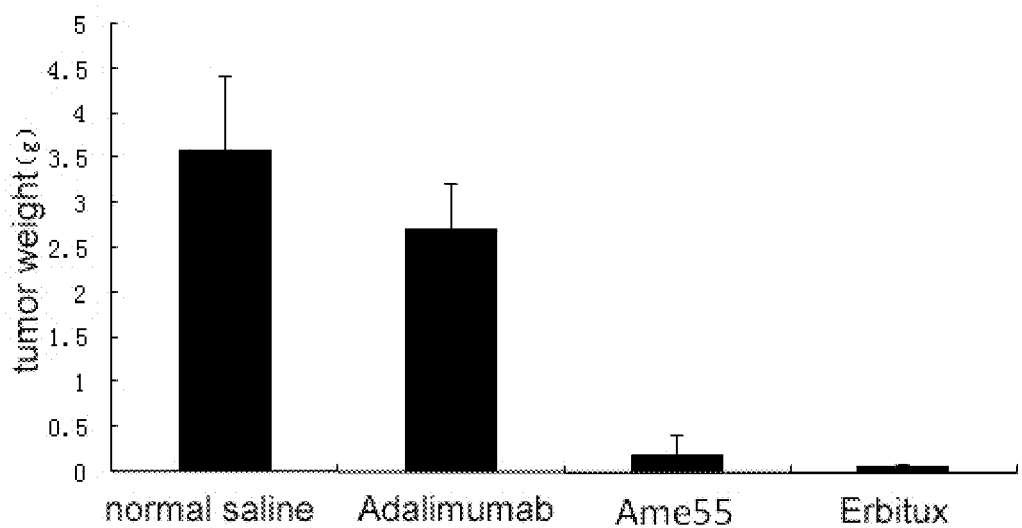
FIG. 12 is a graph showing the inhibition of Ame55 on tumor in A431 tumor-bearing mice.
Figure 13:
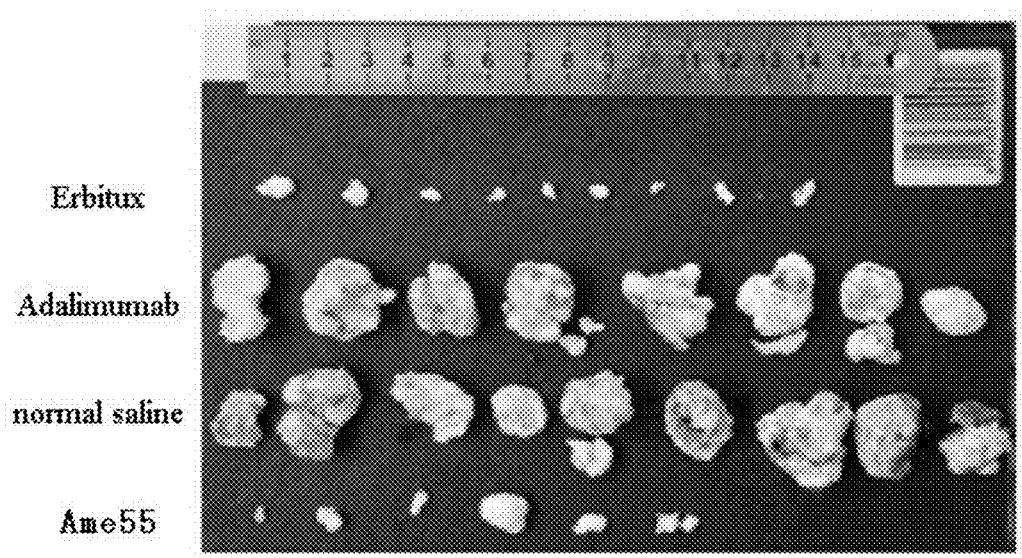
FIG. 13 is a graph showing the inhibition of Ame55 on tumor in A431 tumor-bearing mice.

A431 cell transplantation tumor was adopted as research object to evaluate the inhibition effect of Ame55 on the tumor growth of a tumor-bearing mouse. Experimental results show that Ame55 has significant inhibition effect on the growth of the A431 transplantation tumor at the dose of 1 mg/mouse (FIG. 11); and the tumor weight results, which were obtained after continuously administering for 6 times and stopping administration for observation 4 weeks, showed that: the average tumor weight of the control group was 3.65 g, the average tumor weight of the Ame55 group was 0.32 g, and its tumor inhibition rate was above 90% (FIGS. 12 and 13).

Example 5

Evaluation Method for Ame55 Light and Heavy Chain Variable Region Mutant

1. Alanine Scanning

Site-directed mutagenesis primers were designed respectively to perform alanine scanning on CDRL1, CDRL3, CDRH2 and CDRH3, and if it is alanine at the site, the alanine was mutated into Gly and Ser respectively. The method used is a site-directed mutagenesis method for plasmid, with reference to the document [WANG Ronghao, CHEN Ruichuan, LIU Runzhong. A modified method of quickly site-directed mutagenesis. Journal of Xiamen University (Natural Science), 2008, Vol 47, sup 2, 282-285].

2. Detection of Antibody Affinity Via ForteBio QKe

EGFR-Fc fusion protein was biotinylated using a biotin kit, and the biotinylated EGFR-Fc was diluted with PBS to a concentration of 100 nM, and coated onto the surface of a streptavidin sensor for 20 min. The sensor was cleaned using HEPES EP for 5 min, and mutant antibody and parent antibody Ame55 to be detected were placed in detection pores at a concentration of 20 nM into detection holes, and bound to EGFR-Fc on the surface of the cleaned streptavidin sensor for 10 min After the binding reached balance, the complex was dissociated in HEPES EP, wherein the dissociation time was 20 min. ForteBio software package was adopted to perform affinity analysis.

3. Tumor Inhibition Activity Comparison of Mutant and Parent Antibody

The experimental method was the same as in Example 4, and the group and the dosage were set as follows: normal saline control, Erbitux control, Ame55 parent antibody control and various Ame55 mutant antibodies (Ametumumabs) such as AmeA1C1, AmeA1C3, AmeA1C3-HI2, AmeA2, AmeA2C1, AmeA2C3, AmeA2C3-HI2, total 10 groups, 8 mice for each group, dose for administration was 0.2 mg/mouse, 3 d/time), wherein the administration was performed for 6 times, and 6 days after stopping drug administration, the mice were sacrificed to collect tumors for weighing.

II. Results

1. Affinity Analysis of Mutants

Based on Ame55 amino acid sequence, the mutations were performed for partial amino acids of the light and heave chain variable regions and framework regions. The mutants were designed by alanine scanning and site-directed mutation. A ForteBio $QK^e$ protein molecule interaction system was used to further screen and evaluate the affinity of the mutants. Results showed (FIG. 1) that, compared to parent antibody Ame55, multiple amino acid sites of light chains CDR1 and CDR3 and heavy chains CDR2 and CDR3 regions are all essential for maintaining the binding capability of the antibody to EGFR, for which the reason may be that the amino acid at the site directly participates the interaction, or that the amino acid at the site is essential for maintaining the correct whole space structure of the antibody. Among the sites where amino acids were modified, amino acids of the light chain at site 26 and site 89, and amino acids of the heavy chain at site 54 and site 107 are most important. After single amino acid substitution firstly, the present invention found that after the amino acid of the light chain at site 89 was modified from Val into Ala or Ser, the affinity was increased by 4 times, and after further combining Gly or Lys of the light chain at site 26, the affinity was further improved by above 5 times compared to the affinity of the parent antibody; or after the amino acids of the heavy chain at site 54 an site 107 were substituted for Ser respectively, and were expressed in combination with light chain 89A/S, the affinities of the antibodies were improved at different degrees based on 89A/S. In order to further confirm the effect of the affinity improvement on the bioactivity of the antibody, further, in-vivo activity of the following 7 mutant antibodies were further evaluated: AmeA1C1 (the mutated light chain has Gly at site 26 and Ser at site 89), AmeA1C3 (the mutated light chain has Lys at site 26 and Ser at site 89), AmeA1C3-HI2 (the mutated light chain has Lys at site 26 and Ser at site 89, whilst the mutated heavy chain has Ser at site 107), AmeA2 (the mutated light chain has Aly at site 89), AmeA2C1 (the mutated light chain has Gly at site 26 and Ala at site 89), AmeA2C3 (the mutated light chain has Lys at site 26 and Ala at site 89), and AmeA2C3-HI2 (the mutated light chain has Lys at site 26 and Ala at site 89, whilst the mutated heavy chain has Ser at site 107).

2. Tumor Inhibition Activity Comparison Between Mutants and Ame55

Figure 14A:
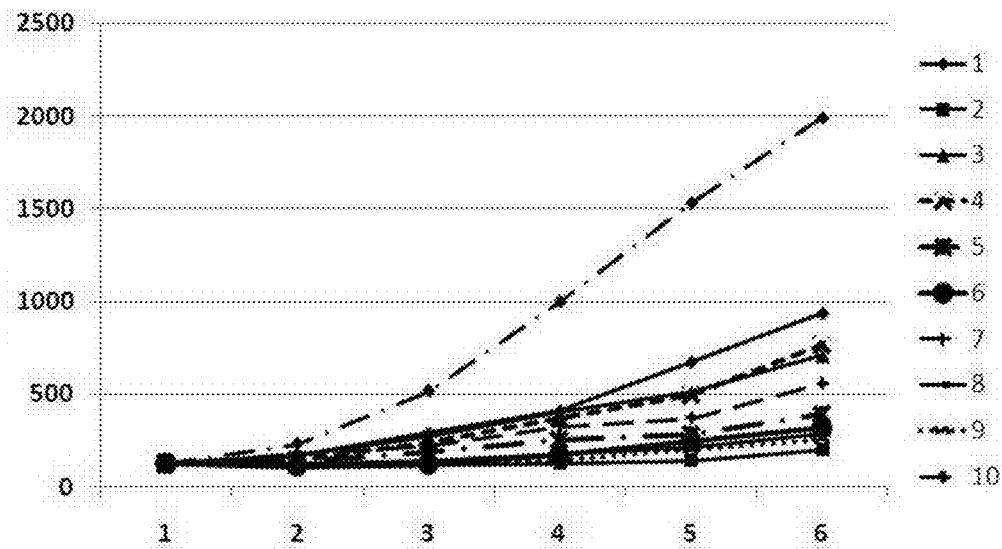
FIG. 14 is a graph showing the comparison of inhibitory activity of Ame55 and mutant antibodies thereof on tumor growth in tumor-bearing mice, A: dynamic observation of tumor volume; B: statistical results of tumor weight measurement. 1: Ame55; 2: AmeA1C1; 3: AmeA1C3; 4: AmeA1C3-HI2; 5: AmeA2; 6: AmeA2C1; 7: AmeA2C3; 8: AmeA2C3-HI2; 9: Erbitux; 10: IgG control.
Figure 14B:
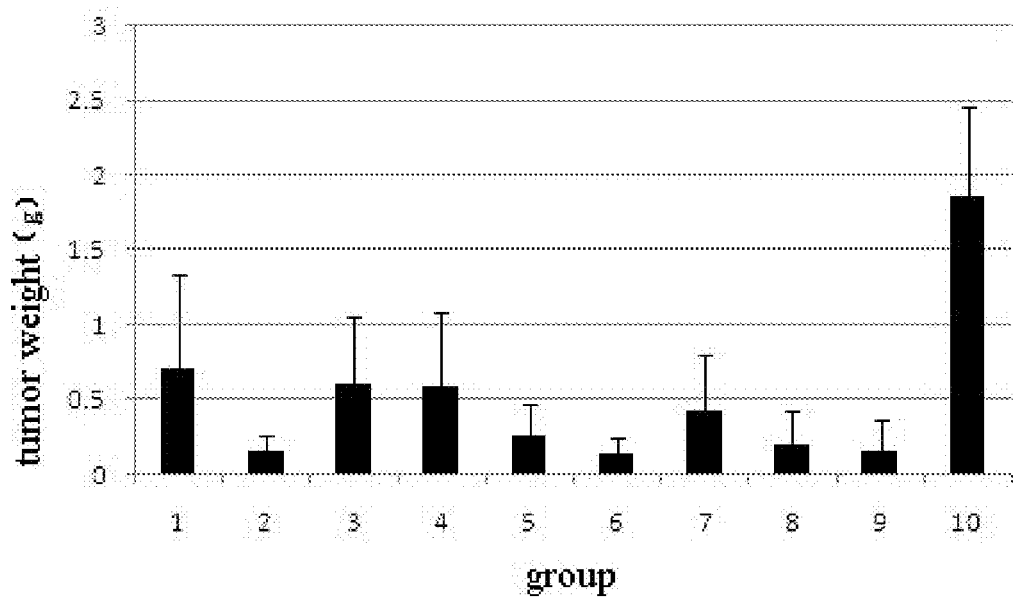

In order to further evaluate the difference between the activities of the mutants and the parent antibody, the dose for administration was decreased to a low dosage of 0.2 mg/mouse, and the tumor inhibition activities of several mutants with affinity improved at different degrees and parent antibodies were compared on mice with transplantation tumors. Results showed that the average tumor weight of the control antibody group was 1.854 g; at the administration dosage of 0.2 mg/mouse, the tumor inhibition activity of the parent antibody Ame55 group (average tumor weight is 0.71 g) is decreased to about 60%; moreover, the tumor inhibition activity of the mutant antibody is obviously better than that of the parent antibody, and the tumor inhibition rates thereof are 67%-93% respectively, and the activities of some antibodies are equivalent to that of commercial antibody Erbitux (tumor inhibition rate of 91%). The results indicate that the improvement of the mutant affinity is indeed beneficial for the improvement of the in-vivo bioactivity thereof. The tumor growth conditions and the statistic analysis on tumor weight of different groups are shown in FIG. 14.

TABLE 1 statistical table for Ame55 mutant affinity change condition

| Light chain | | Heavy chain | |
| --- | --- | --- | --- |
| Mutation site | Affinity change | Mutation site | Affinity change |
| 13A | 1 | 50A | Not binding |
| 26G(C1) | 0.5 | 50R | Not binding |
| 26N(C2) | 1 | 51A | >10 |
| 26K(C3) | 0.3 | 52A | Not binding |
| G28P | >100 | 52D | >10 |
| 29E | >100 | 53A | 5 |
| 32I | 1 | 54A | >10 |
| 32V | 2 | 54S | 0.5 |
| 33Y | 2 | 55A | >100 |
| 51G | 1 | 56A | 1 |
| 55P | 2 | 57A | Not binding |
| 88Q | 2 | 57Y | Not binding |
| 88A | >10 | 58A | >10 |
| 88Y | 5 | 59A | >10 |
| 88L | 5 | 59N | >10 |
| 88G | 3 | 60A | 5 |
| 88N | >10 | 66H | 1 |
| 89S(A1) | 0.5 | 99A | >10 |
| 89A(A2) | 0.25 | 99S | >10 |
| 89L | 5 | 100A | 5 |
| 90A | >10 | 101A | 4 |
| 91A | >10 | 102A | Not binding |
| 92A | 2 | 103A | Not binding |
| 92S | 4 | 104A | 3 |
| 92P | 1 | 105A | >10 |
| 93A | >10 | 106A | >10 |
| 94A | >10 | 107G | 1.5 |
| 95A | >10 | 107S | 0.2 |
| 95S | >10 | 108A | 5 |
| 96A | >10 | | |
| 97A | >10 | | |
| 26G + 89S | <0.3 | | |
| 26K + 89S | <0.2 | | |
| 26G + 89A | <0.2 | | |
| 26K + 89A | <0.1 | | |

Note:
comparing mutant antibody with parent antibody, the affinity of the parent antibody is set to be 1, and the reduction fold of the affinity is calculated.

Example 6

Detection of Specific Binding Capability of Ame55 Light Chain to EGFR

Figure 15:
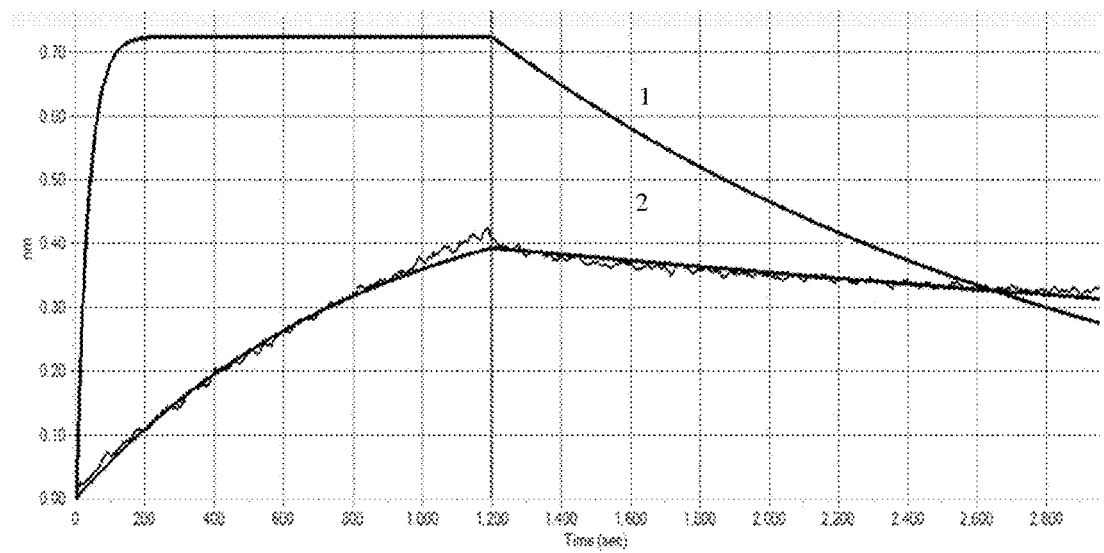
FIG. 15 is graph showing affinity test of mutant Ame-9B formed by combining Ame55 light chain with another unrelated heavy chain.

In order to verify whether the Ame55 light chain has specific binding capability to EGFR, an individual light chain of Ame55 (the amino acid sequence of SEQ ID NO.20) was combined with an antibody heavy chain from VH3 germline gene family (the sequence is shown by SEQ ID NO. 22) in the example, and expressed tansiently in an HEK293 transient expression system, so as to obtain another new antibody Ame-9B containing Ame55 light chain by purifying with Protein A column. The binding capability of Ame-9B to EGFR was detected via a Fortebio protein interaction system, with reference to Example 5 for specific method. Results showed that although the affinity of Ame-9B was decreased (by about 6 times), Ame-9B still maintained the binding capability to EGFR (refer to FIG. 15).

INDUSTRIAL APPLICATION

The binding affinity of the antibody of the present invention for human EGFR is no more than 1 nM, and the affinity of the mutants thereof is no more than 10 nM; and the identification of the immunity activity and bioactivity of antibody protein IgG is completed, verifying that the antibody of the present invention has good bioactivity of inhibiting the tumor growth of EGFR expressing cell A431 tumor-bearing model mouse. The antibody of the present invention provides specific antibody drugs for preventing and treating EGFR targeted tumor and other diseases such as inflammation and autoimmune diseases.

What is claimed is:

1. A human anti-human EGFR antibody wherein:
    (a) the antibody comprises a light chain variable region comprising the amino acid sequence of SEQ ID NO: 20 and a heavy chain variable region comprising the amino acid sequence of SEQ ID NO: 21,
    (b) the antibody comprises a light chain variable region comprising the amino acid sequence of SEQ ID NO: 20 and a heavy chain variable region comprising the amino acid sequence of SEQ ID NO: 21, wherein the amino acid of position 26 of SEQ ID NO: 20 is replaced with Gly and the amino acid of position 89 of SEQ ID NO: 20 is replaced with Ser,
    (c) the antibody comprises a light chain variable region comprising the amino acid sequence of SEQ ID NO: 20 and a heavy chain variable region comprising the amino acid sequence of SEQ ID NO: 21, wherein the amino acid of position 26 of SEQ ID NO: 20 is replaced with Lys and the amino acid of position 89 of SEQ ID NO: 20 is replaced with Ser,
    (d) the antibody comprises a light chain variable region comprising the amino acid sequence of SEQ ID NO: 20 and a heavy chain variable region comprising the amino acid sequence of SEQ ID NO: 21, wherein the amino acid of position 26 of SEQ ID NO: 20 is replaced with Gly, and the amino acid of position 89 of SEQ ID NO: 20 is replaced with Ala,
    (e) the antibody comprises a light chain variable region comprising the amino acid sequence of SEQ ID NO: 20 and a heavy chain variable region comprising the amino acid sequence of SEQ ID NO: 21, wherein the amino acid of position 26 of SEQ ID NO: 20 is replaced with Lys and the amino acid of position 89 of SEQ ID NO: 20 is replaced with Ala,
    (f) the antibody comprises a light chain variable region comprising the amino acid sequence of SEQ ID NO: 20 and a heavy chain variable region comprising the amino acid sequence of SEQ ID NO: 21, wherein the amino acid of position 26 of SEQ ID NO: 20 is replaced with Lys, the amino acid of position 89 of SEQ ID NO: 20 is replaced with Ser, and the amino acid of position 107 of SEQ ID NO: 21 is replaced with Ser,
    (g) the antibody comprises a light chain variable region comprising the amino acid sequence of SEQ ID NO: 20 and a heavy chain variable region comprising the amino acid sequence of SEQ ID NO: 21, wherein the amino acid of position 89 of SEQ ID NO: 20 is replaced with Ala,
    or
    (h) the antibody comprises a light chain variable region comprising the amino acid sequence of SEQ ID NO: 20 and a heavy chain variable region comprising the amino acid sequence of SEQ ID NO: 21, wherein the amino acid of position 26 of SEQ ID NO: 20 is replaced with Lys, the amino acid of position 89 of SEQ ID NO: 20 is replaced with Ala, and the amino acid of position 107 of SEQ ID NO: 21 is replaced with Ser.

2. The antibody according to claim 1, wherein the antibody is selected from the group consisting of single chain antibodies, Fabs, and intact antibody immunoglobulins: IgG1, IgG2, IgA, IgE, IgM, IgG4, and IgD.

3. A method of treating a tumor expressing EGFR comprising administering an antibody according to claim 1 to a subject in need thereof and inhibiting tumor growth.

4. A drug or detection reagent comprising the antibody according to claim 1 combined with one or more antibodies.

5. An antibody targeted drug molecule, comprising the antibody according to claim 1 linked to a cytotoxic agent.

6. The antibody targeted drug molecule according to claim 5 wherein the cytotoxic agent is linked to the antibody by antibody labeling, in-vitro cross-linking or molecular coupling.

7. The antibody targeted drug molecule according to claim 5 wherein the cytotoxic agent comprises chemical molecules, radioactive isotopes, polypeptides, toxins and other substances having the properties of killing cells or inducing apoptosis.

* * * * *